US009581548B2

United States Patent
Cooper et al.

(10) Patent No.: US 9,581,548 B2
(45) Date of Patent: Feb. 28, 2017

(54) METHODS FOR RESOLVING POSITIONS IN FLUORESCENCE STOCHASTIC MICROSCOPY USING THREE-DIMENSIONAL STRUCTURED ILLUMINATION

(71) Applicant: GE Healthcare Bio-Sciences Corp., Piscataway, NJ (US)

(72) Inventors: Jeremy Cooper, Issaquah, WA (US); William M. Dougherty, Issaquah, WA (US)

(73) Assignee: GE HEALTHCARE BIO-SCIENCES CORP., Marlborough, MA (US)

(*) Notice: Subject to any disclaimer, the term of this patent is extended or adjusted under 35 U.S.C. 154(b) by 0 days.

(21) Appl. No.: 14/430,147

(22) PCT Filed: Sep. 23, 2013

(86) PCT No.: PCT/SE2013/051104
§ 371 (c)(1),
(2) Date: Mar. 20, 2015

(87) PCT Pub. No.: WO2014/046606
PCT Pub. Date: Mar. 27, 2014

(65) Prior Publication Data
US 2015/0241351 A1 Aug. 27, 2015

(30) Foreign Application Priority Data

Sep. 24, 2012 (SE) .................................. 1251069

(51) Int. Cl.
*G01N 21/64* (2006.01)
*G02B 21/14* (2006.01)
(Continued)

(52) U.S. Cl.
CPC ....... *G01N 21/6458* (2013.01); *G01B 11/002* (2013.01); *G01N 21/6486* (2013.01);
(Continued)

(58) Field of Classification Search
CPC ............. G01N 33/5076; G01N 33/582; G01N 33/5005; G01N 33/5011
See application file for complete search history.

(56) References Cited

U.S. PATENT DOCUMENTS

2007/0029462 A1* 2/2007 Perz ...................... G03B 5/00
250/208.1
2008/0032414 A1 2/2008 Zhuang et al.
(Continued)

FOREIGN PATENT DOCUMENTS

DE 102006047912 A1 4/2008
DE 102008009216 A1 8/2009
(Continued)

OTHER PUBLICATIONS

Schermelleh et al., "Subdiffraction multicolor imaging of the nuclear periphery with 3D structured illumination microscopy," Jun. 6, 2008, Science, vol. 320, pp. 1332 1336.*
(Continued)

*Primary Examiner* — Kiho Kim

(57) ABSTRACT

Methods and systems to resolve positions of sample components in fluorescence stochastic microscopy using three-dimensional structured illumination microscopy ("3D-SIM") are disclosed. In one aspect, components of a sample specimen are labeled with fluorophores and weakly illuminated with a frequency of light to stochastically convert a subset of the fluorophores into an active state. The sample is then illuminated with a three-dimensional structured illumination pattern ("3D-SIP") of excitation light that causes the activated fluorophores to fluoresce. As the 3D-SIP is incre-
(Continued)

mentally moved within the volume of the sample and images are recorded, computational methods are used to process the images to locate and refine the locations of the activated fluorophores thereby generating a super-resolution image of sample components.

19 Claims, 31 Drawing Sheets

(51) Int. Cl.

| | |
|---|---|
| *G02B 21/16* | (2006.01) |
| *G02B 21/36* | (2006.01) |
| *G01B 11/00* | (2006.01) |
| *G02B 21/06* | (2006.01) |
| *G02B 27/58* | (2006.01) |

(52) U.S. Cl.
CPC ............ *G02B 21/06* (2013.01); *G02B 21/14* (2013.01); *G02B 21/16* (2013.01); *G02B 21/361* (2013.01); *G02B 21/365* (2013.01); *G02B 21/367* (2013.01); *G02B 27/58* (2013.01); *G01N 2201/0633* (2013.01); *G01N 2201/0636* (2013.01)

(56) References Cited

U.S. PATENT DOCUMENTS

| | | |
|---|---|---|
| 2010/0225911 A1 | 9/2010 | Cohen et al. |
| 2011/0036996 A1* | 2/2011 | Wolleschensky .. G01N 21/6458 250/459.1 |
| 2011/0141483 A1* | 6/2011 | Lee ....................... G06T 7/0057 356/511 |
| 2012/0112095 A1* | 5/2012 | Baer .................. G02B 21/0072 250/459.1 |
| 2013/0229494 A1* | 9/2013 | Dyba ................... G02B 21/367 348/47 |
| 2013/0335819 A1 | 12/2013 | Cooper |

FOREIGN PATENT DOCUMENTS

| | | |
|---|---|---|
| WO | 2006127692 A2 | 11/2006 |
| WO | 2011085766 A1 | 7/2011 |
| WO | 2012118436 A1 | 9/2012 |
| WO | 2012118530 A1 | 9/2012 |

OTHER PUBLICATIONS

Lin et al., "Wide-field super-resolution optical sectioning microscopy using a single spatial light modulator," 2009, Journal or Optics A,: Pure Applied Optics, vol. 11, pp. 1-6.*
"Three Dimensional Super-Resolution Imaging by Stochastic Optical Reconstruction Microscopy" by Huang et al., Science, Feb. 8, 2008, vol. 319, No. 5864, pp. 810-813; whole document.
"Imaging Intracellular Fluorescent Proteins at Nanometer Resolution" by Betzig et al., Science, vol. 313, No. 5793 pp. 1642-1645; whole document.
International Search Report and Written Opinion for International Application PCT/SE2013/051104, mail date Feb. 21, 2014, 9 pages.
Supplementary European Search Report regarding EP Application No. 13839081, dated Jun. 3, 2016, 8 pages.
Lemmer et al., "SPDM: light microscopy with single-molecule resolution at the nanoscale", Applied Physics B; Lasers and Optics, Springer, Berlin, DE, vol. 93, No. 1, Sep. 4, 2008, pp. 1-12.

\* cited by examiner

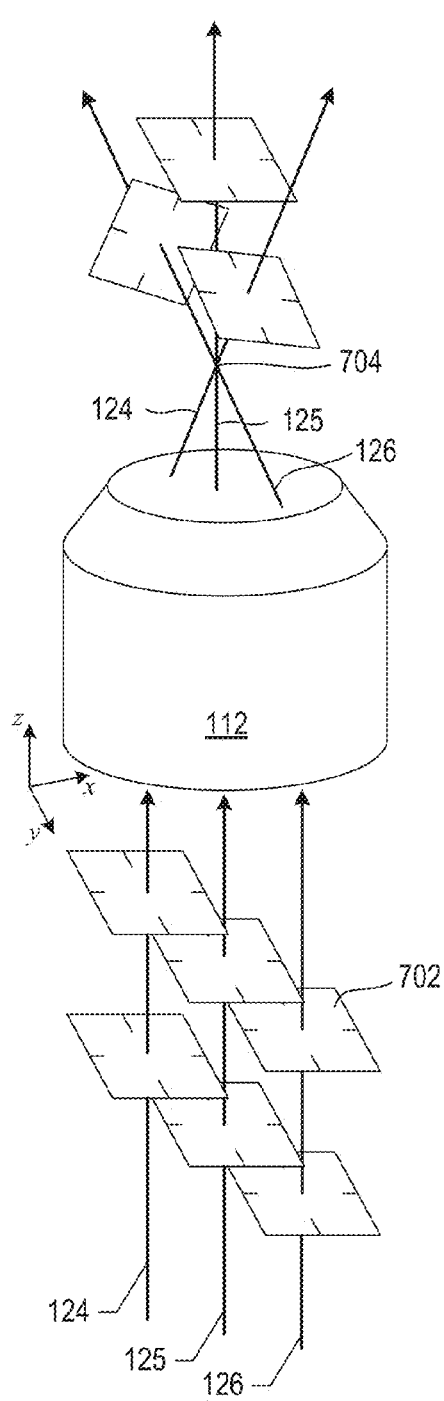
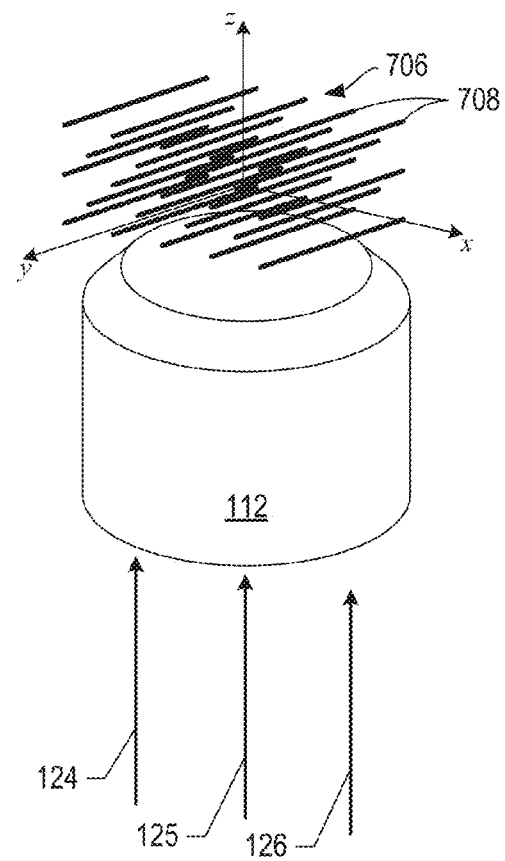
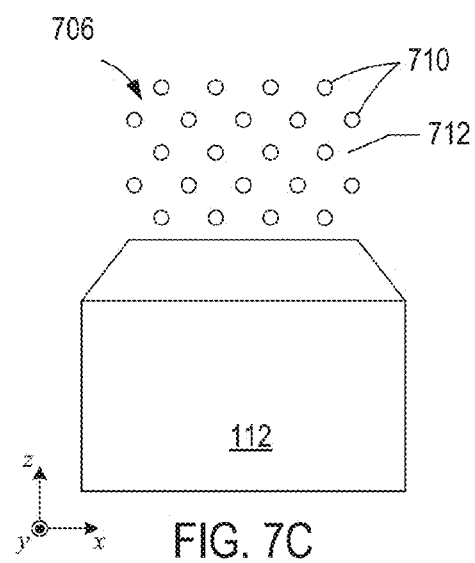
FIG. 7A
FIG. 7B
FIG. 7C

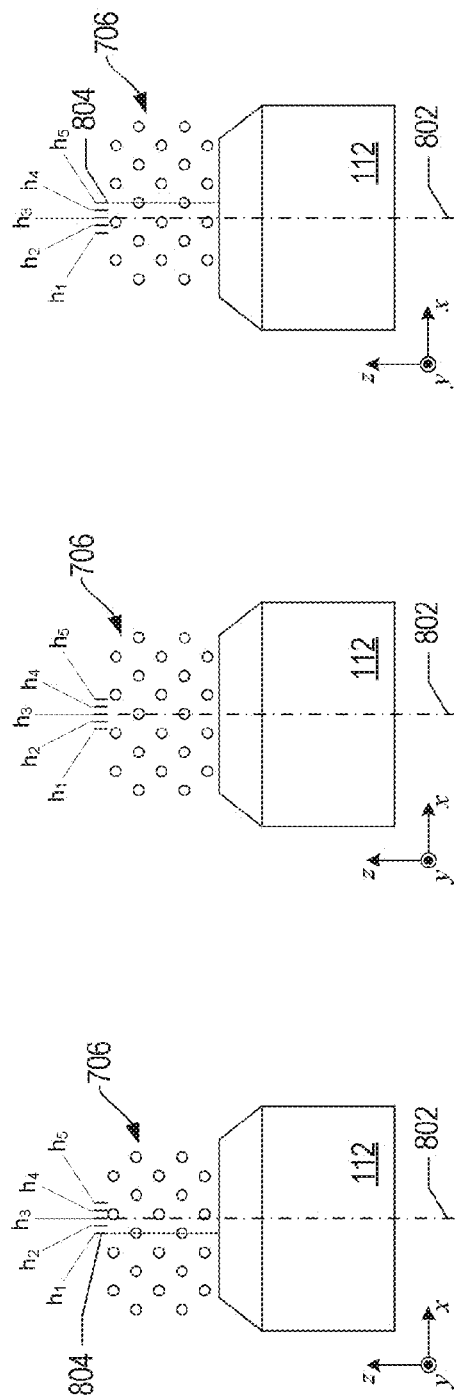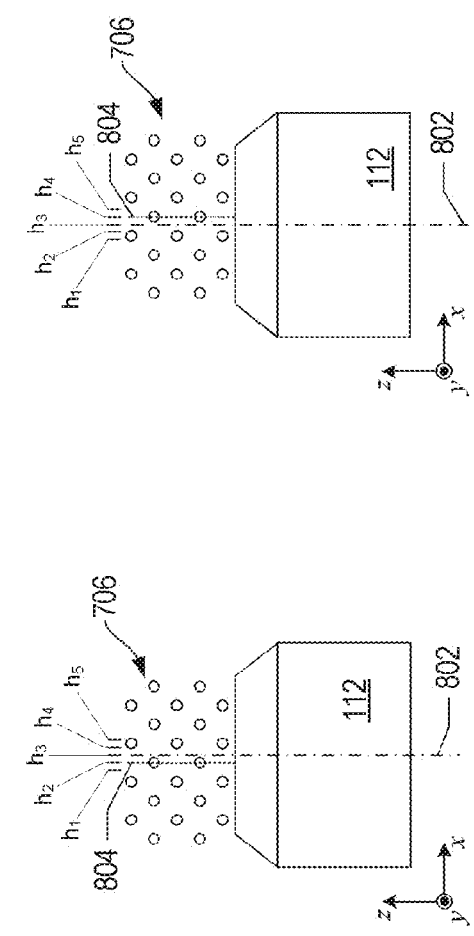

METHODS FOR RESOLVING POSITIONS IN FLUORESCENCE STOCHASTIC MICROSCOPY USING THREE-DIMENSIONAL STRUCTURED ILLUMINATION

This application is a filing under 35 U.S.C. 371 of international application number PCT/SE2013/051104, filed Sep. 23, 2013, which claims priority to Swedish application number 1251069-9, filed Sep. 24, 2012, the entire disclosures of each of which are hereby incorporated by reference.

TECHNICAL FIELD

This disclosure relates to structured illumination microscopy.

BACKGROUND

Fluorescence microscopy is widely used in the biological sciences to study the three-dimensional interior of cells and organisms and to visualize particular biomolecules with specificity through fluorescent labeling. However, one of fluorescence microscopy's greatest weaknesses is moderate spatial resolution, which is fundamentally limited by the wavelength of light. The typical wide-field light microscope has another weakness in that it does not gather sufficient complete information about a sample to allow true three-dimensional imaging, which is called the missing cone problem. The manifestation of the missing cone problem in the raw image data, which are acquired as a sequence of two-dimensional images, often referred to as sections with different focus, is that each section of the data contains not only in-focus information from the corresponding section of the sample but also out-of-focus blur from all other sections. Three-dimensional reconstructions from conventional microscope data presently have to rely on a priori constraints, such as the nonnegativity of the density of fluorescent dye, to attempt to compensate for the missing information.

Confocal microscopy is one technique that addresses both weaknesses by using a pinhole aperture to physically block the out-of-focus light from reaching the detector. Confocal microscopy provides true three-dimensional imaging and at the same time extends resolution somewhat beyond the conventional limit, both axially (i.e., depth) and laterally. The improvement of lateral resolution, however, only takes place when a small pinhole is used, but by using a small pinhole much of the in-focus light is discarded along with the unwanted out-of-focus light. In practice, it is rarely advantageous to use such a small pinhole given the weak fluorescence of typical biological samples and the low sensitivity of detectors normally used in confocal microscopes. The detrimental loss of in-focus light usually outweighs any resolution benefits. As a result, typical confocal microscopes are operated with wider pinholes, producing a lateral resolution that is only a marginal improvement over that provided by conventional wide-field fluorescence microscopes.

In recent years, it has been demonstrated that it is possible to double the lateral resolution of the fluorescence microscope without significant loss of light using spatially structured illumination light to frequency-mix high resolution information into the optical passband of the microscope. In particular, three-dimensional structured illumination microscopy ("3D-SIM") achieves improvement in lateral and axial resolution by a factor of two when compared to confocal microscopy. Because 3D-SIM requires no specialized fluorescent dyes or proteins, biologists achieve high resolution with 3D-SIM and retain convenient and familiar fluorescence labeling techniques. Multiple images of the subject are made by moving three-dimensional structured illumination pattern through the sample. Higher resolution is achieved by solving a system of equations to restore the fine spatial detail normally blurred by diffraction. Even with the improvements in lateral and axial resolution offered by 3D-SIM, scientists, engineers, and microscope manufactures continue to seek data processing methods and microscopy systems that increase the lateral and axial resolution of sample components using fluorescence microscopes.

DESCRIPTION OF THE DRAWINGS

FIGS. 7A-7C show creation of a three-dimensional structured illumination pattern.

FIGS. 8A-8E show an example of stepping a three-dimensional structured illumination pattern stepped perpendicular to an optical axis of an objective lens.

DETAILED DESCRIPTION

Figure 1:
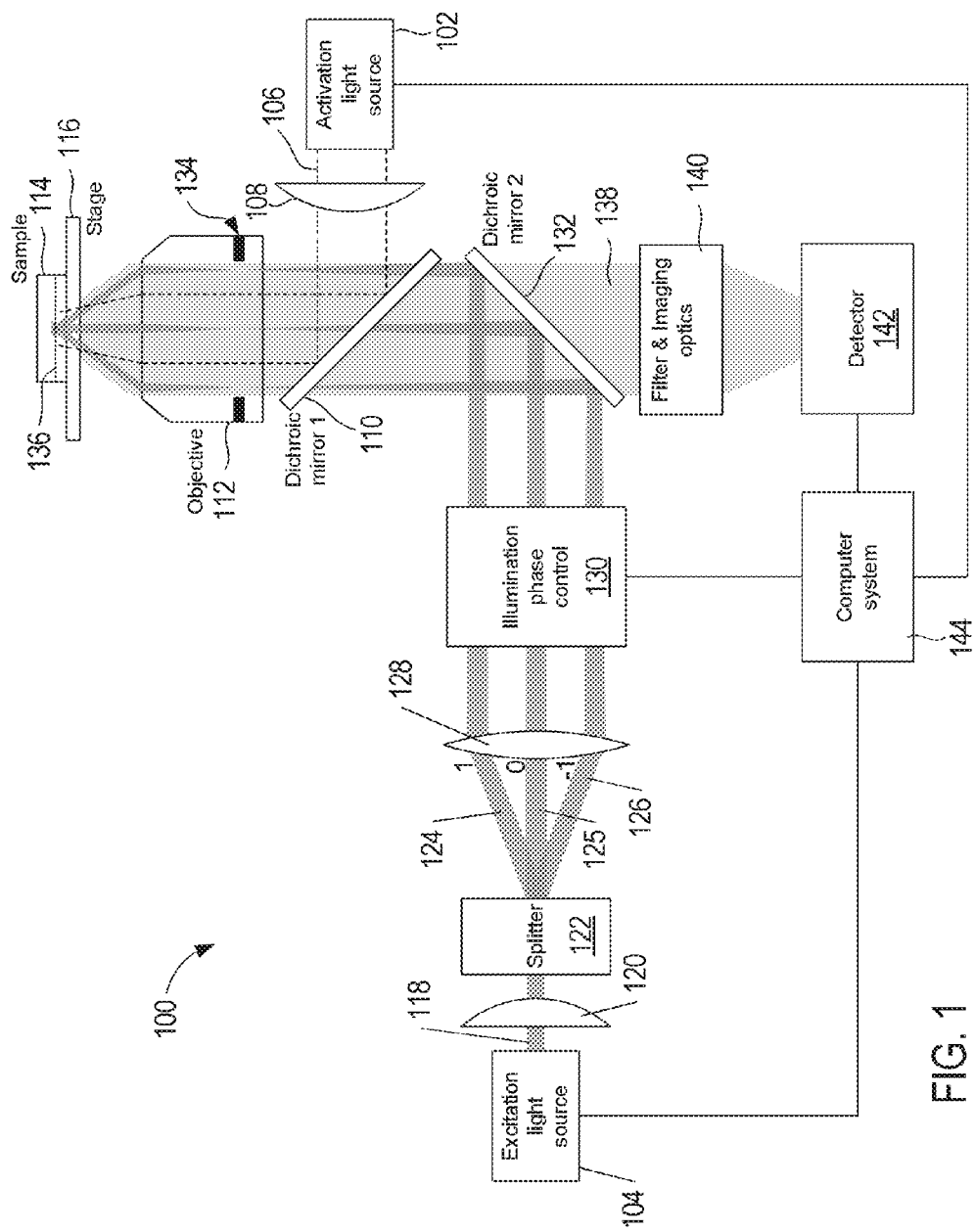
FIG. 1 shows a schematic representation of an example fluorescence microscope.

Methods and systems to resolve positions of sample components in fluorescence stochastic microscopy using three-dimensional structured illumination microscopy ("3D-SIM") are disclosed. The fluorescence intensity response of individual fluorophores to a time-varying local structure of a three-dimensional structured illumination pattern ("3D-SIP") enables lateral and axial resolution that is comparable to or better than the lateral super-resolution provided by stochastic fluorescence methods alone. In one aspect, a sample is labeled with fluorophores of sufficient density to ensure that, when the positions of the fluorophores are accurately determined, those positions produce an image of a structure, component, or organelle of interest to the fluorescence microscopist. Initially, the fluorophores are in a non-fluorescing, dark state. The sample is weakly illuminated with a frequency of light in order to stochastically convert a subset of the fluorophores from the dark state to an active state. Activation is carried out with a weak illumination in order to ensure that the average spacing between fluorophores is greater than the diffraction-limited distance (i.e., about 200 nm). The sample is then illuminated with a 3D-SIP of excitation light that causes the activated fluorophores to fluoresce. As the 3D-SIP is incrementally moved within the volume of the sample and images are recorded, computational methods are used to process the images to locate and refine the locations of the activated fluorophores.

According to one embodiment there is provided a method for determining coordinate positions of light-emitting particles that label at least one component of a sample specimen using a microscope, the method comprising:
  activating a subset of the light-emitting particles;
  capturing a series of images of the light emitted from the subset of particles illuminated with excitation light in a three-dimensional structured illumination pattern;
  generating a resolved image of the light-emitting particles from the series of images; and
  repeatedly activating, illuminating, capturing and generating to obtain a number of resolved images that are processed to obtain a super-resolution image of the at least one component.

The step of activating the subset of particles may further comprise illuminating the sample with low-intensity activation light that stochastically activates the subset of light-emitting particles. The step of capturing the series of images may further comprise generating the illumination pattern from at least three beams of coherent excitation light transmitted through an objective lens to intersect within the sample. The step of capturing a series of images may further comprise changing position of the illumination pattern prior to capturing each image in the series, and changing the position of the illumination pattern may further comprise rotating the illumination pattern or translating the illumination pattern. The method may further comprise photobleaching the subset of light-emitting particles in the activated state.

The step of generating the resolved image may further comprise:
  summing the series of images to generate a summed image of spots;
  determining centroid positions of the spots; and
  resolving spot centroid positions to generate the resolved image.

The method may further comprise discarding image data associated with inconsistent image results for single fluorophores. In the method, the number of resolved images may be processed to obtain the super-resolution image further comprising summing the resolved images to generate the super-resolution image.

There is further provided a method for generating a super-resolution image of a sample specimen using a microscope, the method comprising:
  separately activating different subsets of light-emitting particles attached to components of the sample;
  generating a series of images for each subset of activated particles by repeatedly illuminating the sample with excitation light in a three-dimensional structured illumination pattern and capturing an image of the light emitted from the subset of particles for the illumination pattern in different positions within the sample;
  combining the series of images to generate a resolved image for each subset of activated particles; and
  combining the resolved images to generate a super-resolution image of the sample.

The step of activating different subsets of particles may further comprise illuminating the sample with low-intensity activation light to stochastically activate a subset of light-emitting particles. The step of illuminating the sample with excitation light in a three-dimensional structured illumination pattern may further comprise interfering at least three beams of coherent excitation light that passes through an objective lens to intersect within the sample.

The step of capturing an image of the light emitted from the subset of particles for the illumination pattern in different positions may further comprise rotating the illumination pattern, or translating the illumination pattern to a different lateral position for each image. The step of capturing an image of the light emitted from the subset of particles for the illumination pattern in different positions may further comprise moving the illumination pattern to a different axial position for each image.

The method may further comprise photobleaching each subset of light-emitting particles in the activated state after each resolved image is generated.

The step of generating the resolved image may further comprise:
  summing the series of images to generate a summed image of spots;
  determining centroid positions of the spots; and
  resolving spot centroid positions to generate the resolved image.

The method may further comprise discarding image data associated with inconsistent image results for single fluorophores.

The step of combining the resolved images to generate the super-resolution image may further comprise summing the resolved images.

Fluorescent Microscope

FIG. 1 shows a schematic representation of an example fluorescence microscope 100. There are many different types of fluorescent microscopes and corresponding optical paths. The microscope 100 is not intended to represent the optical paths within all the different variations of instruments used in microscopy, but is instead intended to illustrate the layout of components used to implement fluorescence stochastic microscopy and 3D-SIM microscopy described in greater detail below. The microscopy 100 includes a first activation light source 102 and an excitation light source 104. The light source 102 emits a low-intensity, substantially monochromatic beam of light 106 that is transmitted through a lens or series of lenses 108 that collimate the beam 106. The beam 106 is subsequently reflected from a first dichroic mirror 110 to enter an objective lens 112, which focuses the beam 106 in a region of a sample 114 supported by a stage 116. The low-intensity, short-duration light of the beam 106 stochastically excites a relatively small number of fluorophores into an active state.

The light source 104 emits a high-intensity, substantially monochromatic beam 118 of coherent light that is transmitted through a lens or a series of lenses 120 that collimate the beam 118. The beam 118 can also be output from the source 104 with a particular polarization. The beam 118 then passes through a splitter 122 that splits the beam into at least three separate coherent beams 124-126. For example, the splitter 122 can be a one-dimensional, transmissive diffraction grading that splits the beam 118 into three divergent, co-planar coherent beams 124-126 referred to as the $0^{th}$, $+1^{st}$, and $-1^{st}$ order diffracted beams, respectively. The splitter 122 can be any one of a variety of different types of transmissive gratings. For example, the splitter 122 can be a one-dimensional transmissive grating composed of a transparent plate of glass with a series of substantially parallel grooves formed in one surface of the grating or the splitter 122 can be an opaque plate with a series of substantially parallel thin slits. Alternatively, the splitter 122 can be two or more beamsplitters arranged to split the beam 118 into three or more separate coherent beams. The three beams 124-126 pass through a lens or a series of lenses 128 that reorient the beams 124-126 so that the beams lie in the same plane with the $+1^{st}$ and $-1^{st}$ order diffracted beams 124 and 126 oriented nearly parallel to the $0^{th}$ order diffracted beam 125. In the example of FIG. 1, the beams 124-126 pass through an illumination phase control ("IPC") 130 that controls the phase of one or more of the beams 124-126. Examples of IPCs are described PCT/SE2012/050227 owned by Applied Precision Inc. The beams 124-126 are then reflected off of a second dichroic mirror 132 and refocused into the back focal plane 134 of an objective lens 112. The objective lens 112 recollimates the beams 124-126 to intersect near a focal plane 136 in the sample 114. The beams 124-126 interfere and generate a high-contrast, three-dimensional, structured illumination pattern within a volume of the sample 114, as described in greater detail below in a subsection titled Three-dimensional Structured Illumination Microscopy.

The sample 114 may include a number of different types of components, such as organelles of a cell, and each type of component can be labeled with a different type of fluorescent probe. Each type of probe is designed to bind specifically to a particular component of the sample 114, and each type of fluorophore is bound to a particular type of probe. When the sample 114 is illuminated with a three-dimensional structured illumination pattern with a frequency that causes the activated fluorophores to emit light with a frequency in the visible and near-visible portion of the electromagnetic spectrum, a portion of the fluorescent light emitted from the activated fluorophores is collected and collimated by the objective lens 112 into a beam 138. The dichroic mirrors 110 and 132 allow transmission of the beam 138, and filter and imaging optics 140 filter stray excitation light and focus the beam 138 onto a sensor of a detector 142. The detector 142 can be a photodetector array, CCD camera, or a CMOS camera. The light source 102 can also be controlled to output a substantially monochromatic beam of light that follows the same path as the beam 106 to photobleach activated fluorophores. Use of the light output from the light source 102 to activate and photobleach fluorophores is described in greater detail below in the subsection titled Fluorescence Stochastic Microscopy. As shown in FIG. 1, the first and second light sources 102 and 104, IPC 130, and the detector 142 are connected to a computing system 144. The system 144 controls timing and operation of the light sources 102 and 104, the IPC 130, and the detector 142 and can process the images captured by the detector 142 to resolve the positions of the light emitted from the fluorophores as described in greater detail below.

Fluorescence Stochastic Microscopy

Figure 2:
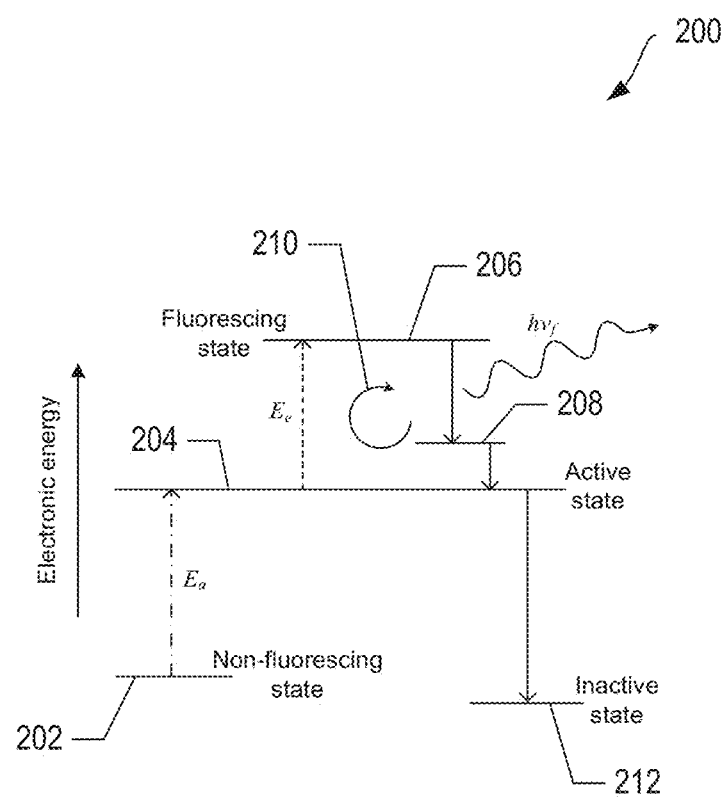
FIG. 2 shows an example of an electronic band diagram.

The light source 102 emits for a brief period of time low-intensity light with an activation frequency that converts a set, or relatively small number of, the fluorophores in the sample 114 into an active state. After the set of fluorophores have been activated, the light source 102 is turned "off" and the light source 104 is turned "on" in order to emit higher intensity light with an excitation frequency that causes those fluorophores already in the active state to fluoresce. FIG. 2 shows an example of an electronic band diagram 200 associated with fluorophores used to label components of a sample. When the fluorophores are introduced to the sample, each type of fluorophore is attached to a probe that binds to a specific component of the sample. The fluorophores are initially in a non-fluorescing, or dark, state 202, which may be a ground state for the fluorophore. The light source 102 emits activation light, as described above with reference to FIG. 1, with an activation frequency, $v_a$, (i.e., electronic energy $hv_a \geq E_a$, where h the Planck constant) for a brief period of time and with a very low intensity in order to stochastically convert a relatively small number of fluorophores into the active state 204. The activation light is turned "off" followed by turning "on" the light source 104 to emit light with an excitation frequency, $v_e$, (i.e., electronic energy $hv_e \geq E_e$) that further excites only the subset of fluorophores already in the active state into a fluorescing state 206. The fluorophores in the fluorescing state emit fluorescent light with a frequency, $v_f$, and electronic energy, $hv_f$, when transitioning to a lower energy intermediate state 208 followed by thermal relaxation back to the active state 204. In certain embodiments, the light source 104 can emit excitation light sufficient to cause the activated fluorophores to undergo hundreds, thousands or more excitation/emission cycles 210. The light source 102 can be used to photobleach the activated fluorophores. Alternatively, the light source 102 can emit light with a third frequency that converts the fluorophores from the active state 204 into the inactive state 212. Converting fluorophores from the active state 204 into the inactive state 212 can be a complete or partial reconfiguring of each activated fluorophore into a molecule that is not able to transition back to the active state or the fluorescing state when illuminated by either of the activation or excitation frequencies.

Figure 3:
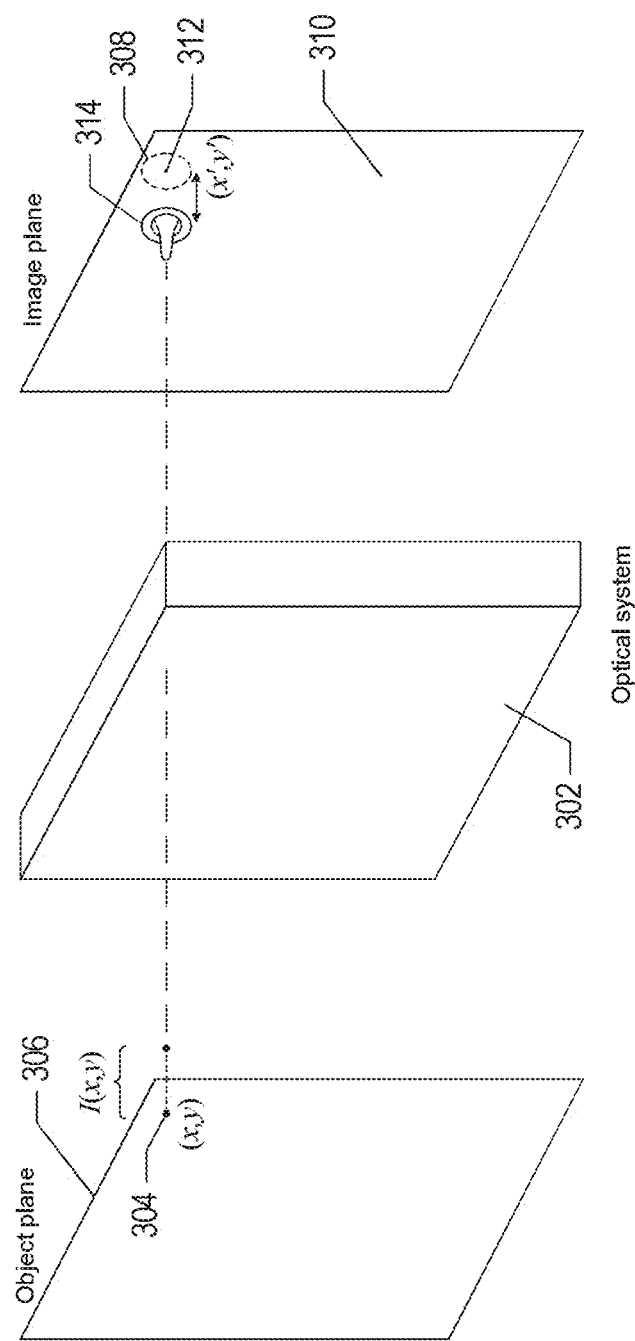
FIG. 3 shows an example optical system of a microscope that receives light output from a point source in an object plane.

Stochastic fluorescence microscopy techniques collect a series of intermediate images of fluorescent light emitted from different subsets of fluorophore-labeled components of a sample over time, provided the emitting fluorophores are separated from one another by distances greater than about 200 nm. In other words, provided the positions of the emitting fluorophores in the sample can be resolved by traditional optical microscopy, the positions of the fluorophores in a sample can be determined, in certain cases, to a resolution of below 10 nm. However, because the fluorescent-emission signal can be interpreted only when the emitting fluorophores are sparsely arranged within the sample, a large number of intermediate images are produced from different subsets of sparse, stochastically distributed, activated fluorophores in order to construct a final image of the sample. Each intermediate image captured by the detector 142 is a diffraction-limited image of a subset of sparsely arranged fluorophores. As the fluorescent light emitted from the fluorophores passes through the optical system of the microscope 100, the light spreads out somewhat in the image plane of the detector 142. The filtering and imaging optics 140 may include a camera lens and other optical components of the microscope 100 that direct and focus light output from an object plane of the sample onto the image plane of the detector 142. When an optical system with a circular aperture receives plane waves output from a point source in the object plane of a sample, such as fluorescent light emitted from a fluorophore, rather than there being a corresponding bright narrowly defined image point in the image plane, the light actually spreads out into a circular spot called an Airy disk composed of alternating light and dark rings. FIG. 3 shows a representation of an example optical system 302 of a microscope that receives light output from a point source (x, y) 304 in an object plane 306 of a sample. For example, the point source 304 can be a fluorescing fluorophore in the focal plane 136 of the sample 114 shown in FIG. 1. The optical system 302 spreads the light out to produce a spot 308 in a corresponding image plane 310 of the detector 142. The light output from the point source 304 has an intensity I(x, y) that is transformed by the optical system 302 into the spot 308 centered about a point (x', y') 312 with a corresponding intensity distribution represented by a symmetrical Airy disk 314 over the spot 308.

Figure 4:
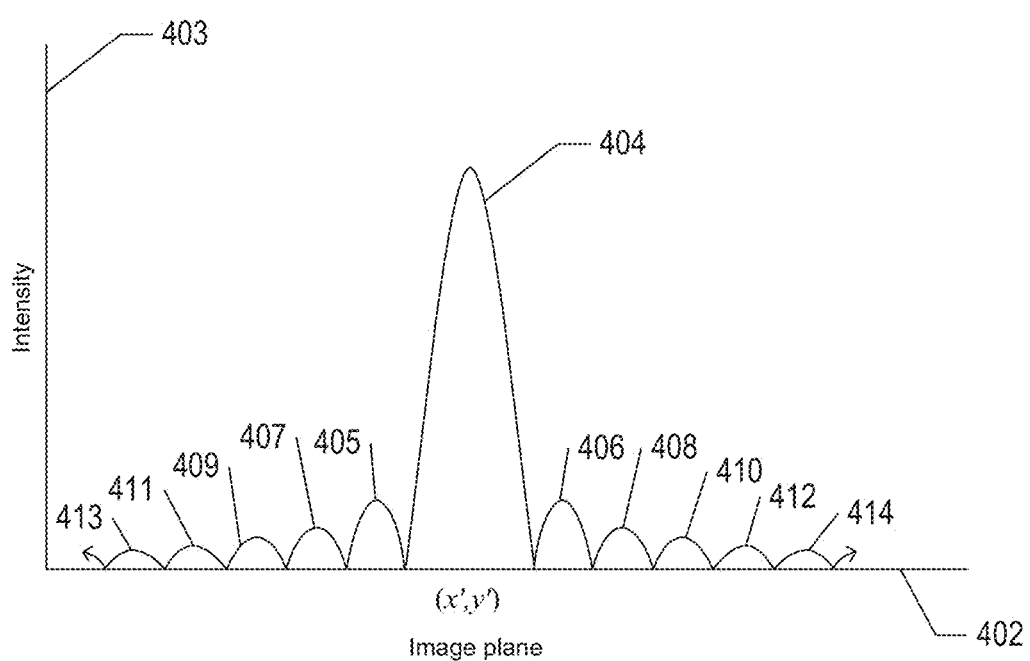
FIG. 4 shows an example intensity distribution of a spot in an image plane.

FIG. 4 shows an example intensity distribution of an Airy disk in one dimension of an image plane. Horizontal axis 402 is a line in the image plane passing through a point (x', y'), such as the point 312 shown in FIG. 3, and vertical axis 403 represents intensity. The Airy disk has a tall, relatively narrow central peak 404 with secondary peaks of decreasing height 405-414 extending outward away from the central peak. The heights of the curves correspond to intensities. Any point on the surface of the Airy disk represents the intensity observed at a corresponding position on the image plane. In other words, an image produced by an optical system of a point source in the object plane appears as a central bright disk, corresponding to the central peak 404 of the Airy disk, with concentric rings of light of increasing radius corresponding to the rings or ridges surrounding the central peak.

Figure 5:
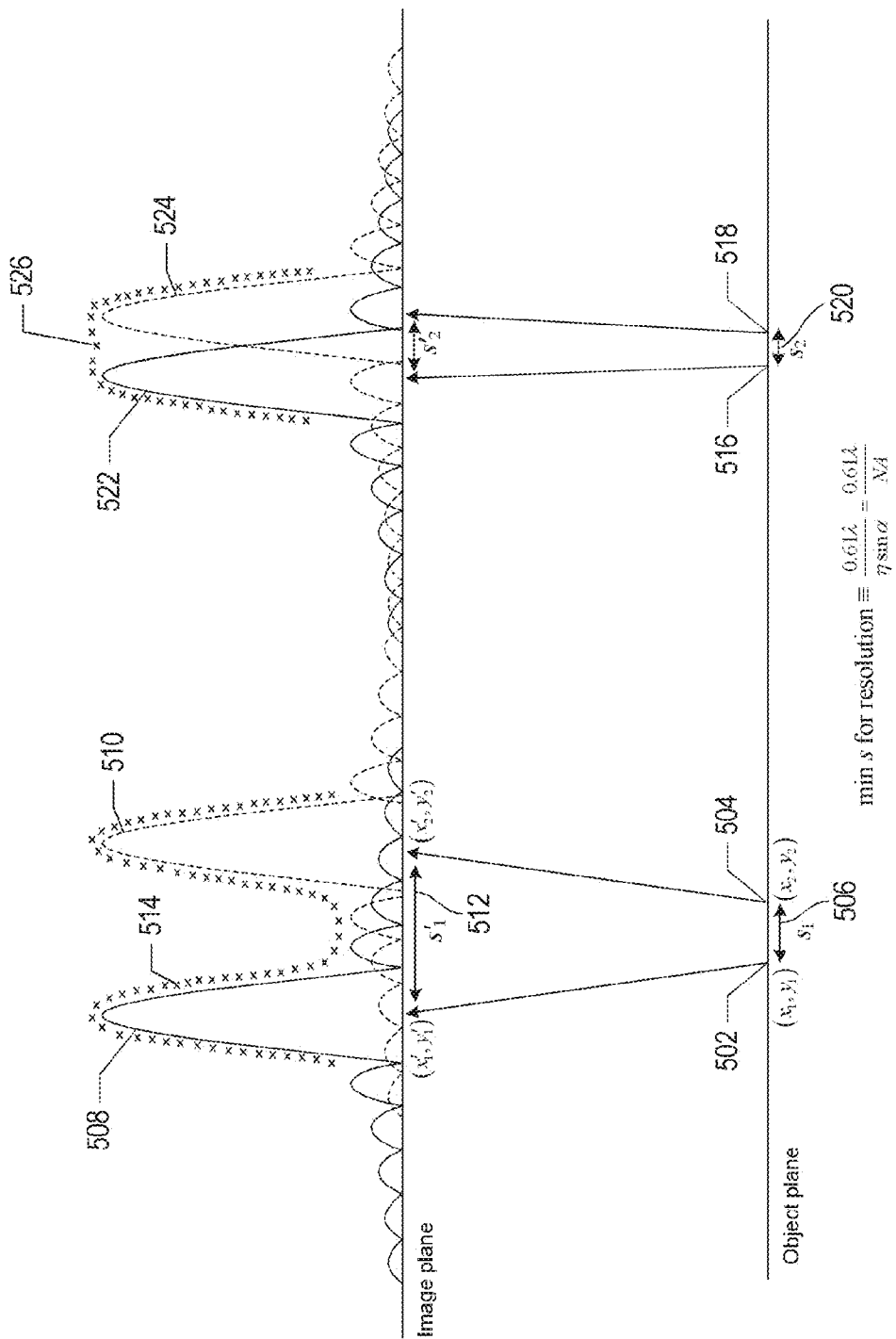
FIG. 5 shows an example of the diffraction limit associated with an optical system.

The radius of the Airy disk determines the overlapping of neighboring Airy disks and therefore the diffraction limit of the image. FIG. 5 shows an example of the diffraction limit associated with an optical system. Consider two points $(x_1, y_1)$ 502 and $(x_2, y_2)$ 504 in an object plane separated by a distance $s_1$ 506. The images of these two points output from an optical system appear as two Airy disks 508 and 510 centered at image points $(x'_1, y'_1)$ and $(x'_2, y'_2)$, respectively. The spreading of light from point sources 502 and 504 into spots with intensity distributions represented by the disks 508 and 510 in the image plane is a diffraction-related phenomenon. When $s_1$ is sufficiently large that the corresponding distance $s'_1$ 512 between the centers of the disk 508 and 510 in the image plane separates the Airy disk so that the sum of the two Airy disks, represented in FIG. 5 by curve 514, remains bimodal, the images of the points 502 and 504 in the image plane can be distinguished from one another. However, when two points 516 and 518 in the object plane are separated by a sufficiently small distance $s_2$ 520 (i.e., $s_2<s_1$), the corresponding images 522 and 524 of the two points in the image plane overlap, with the sum of the two Airy disks, represented by curve 526, merging into a single peak, the two points 516 and 518 cannot be resolved in the image plane. The minimum spacing, or maximum resolution, for traditional optical microscopy is generally regarded as:

$$\frac{0.61\lambda}{n\sin\theta} = \frac{0.61\lambda}{NA}$$

where $\theta$ is the half-angle of the maximum cone of light that can enter or exit the optical system;
$\lambda$ is the wavelength of light;
n is the index of refraction of the medium in which the optical system is operating; and
NA is the numerical aperture of the microscope objective lens.

The minimum spacing, or maximum resolution, in the input image corresponds to spacing between Airy disk at which the first left-hand zero point of the right-hand disk coincides with the first right-hand zero point of the left-hand disk. The minimum separation, or maximum resolution, of any two adjacent fluorescing fluorophores that can be imaged corresponds to about 200 nm for optical microscopy systems. The minimum spacing, or maximum resolution, is referred to as "the diffraction limit," since the Airy disk images of point sources in the image plane arise as a result of diffraction.

In order to obtain a low density of simultaneously activated fluorophores separated by at least 200 nm, the light source 102 emits the activation beam 106 with a very low intensity and for a short period of time so that only a few photons with activation frequency $v_a$, reach the object plane of the sample 114 to excite a small, stochastically-distributed subset of the fluorophores. As a result, the likelihood of any two activated fluorophores being separated by less than 200 nm is very low. When the activated fluorophores are subsequently excited with the excitation light of frequency $v_e$ output from the light source 104, the image captured by the detector 142 is ideally composed of a sparse distribution of non-overlapping spots that can be characterized by Airy disks.

Figure 6:
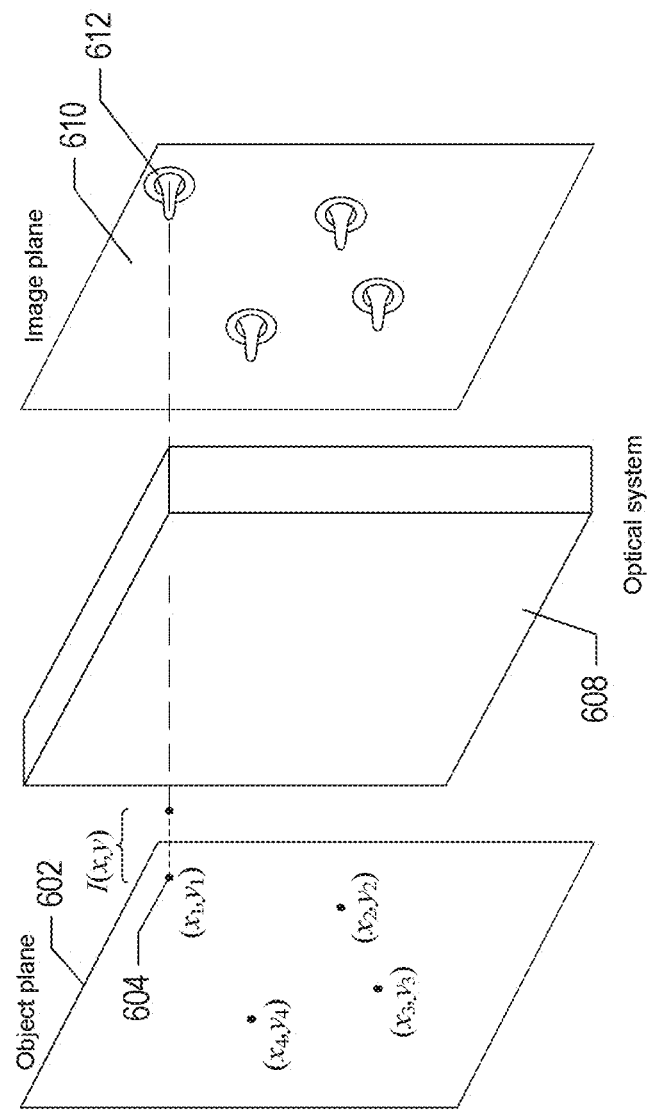
FIG. 6 shows an example of a sparse distribution of fluorescing fluorophores.

FIG. 6 shows an example object plane 602 of a sparse stochastic distribution of four fluorescing fluorophores in an image plane. The sparse stochastic distribution of fluorescing fluorophores in the object plane 602 is produced by activating the sample with a very low intensity beam of activation light followed by exciting the set of activated fluorophores with a three-dimensional interference patter of excitation light as described below in the subsection titled Three-dimensional Structured Illumination Microscopy. The optical system 608 collects the light output from the four fluorescent point sources in the object plane 602 and as the light from the point source passes through the system 608, the light spreads out to produce four corresponding spots in an image plane 610. For example, point source 604 in the object plane 602 corresponds to a spot 612 in the image plane 610. The intensity distribution of each spot in the image plane 610 can be characterized by an Airy disk, as described above. Methods for processing the spots in the image plane 610 to determine and resolve the coordinates of pixels that correspond to the central peak intensity of each spot are described below in the subsection titled Methods for Resolving Centroid Positions.

Three-Dimensional Structured Illumination Microscopy

FIGS. 7A-7C show creation of a three-dimensional structured-illumination pattern ("3D-SIP") from the intersection of coherent beams 124-126. In FIG. 7A, the beams 124-126 are transmitted into the back of the objective lens 112. Because the beams 124-126 originate from a coherent light source 104, the plane waves of the beams 124-126 have identical phases across any plane, such as plane 702, normal to the beam direction. While the beams 124-126 are coherent, each beam may have a different phase displacement than the other two beams. The objective lens 112 focuses the beams to a focal point 704, which changes the direction of the two non-axial beams 124 and 126, as shown in FIG. 7A. As a result, the three plane waves are no longer parallel with wave vectors having different directions and the three sets of plane waves intersect to form a 3D-SIP of bright lines of excitation light that are formed due to constructive interference and are surrounded by dark regions that are formed due to destructive interference. Note that FIGS. 7A-7C, and subsequent figures, include a Cartesian coordinate system that represents the orientations of the 3D-SIP with the bright lines extending in the y-direction and spaced apart in the xz-plane. The Cartesian coordinate system can be used to represent microscope coordinates or relative The z-direction is parallel to the optical axis of the objective lens 112. In the example of FIG. 7B, a stationary 3D-SIP 706 intersects the focal plane of the objective lens 112. Lines 708 represent bright lines of excitation light separated by darker or lower intensity regions. FIG. 7C shows an xz-plane view of the objective lens 112 and an end-on view of the bright lines comprising the 3D-SIP 706. Open circles 710 represent an end-on view of the centers of the bright lines of excitation light within a dark region 712.

Figure 7D:
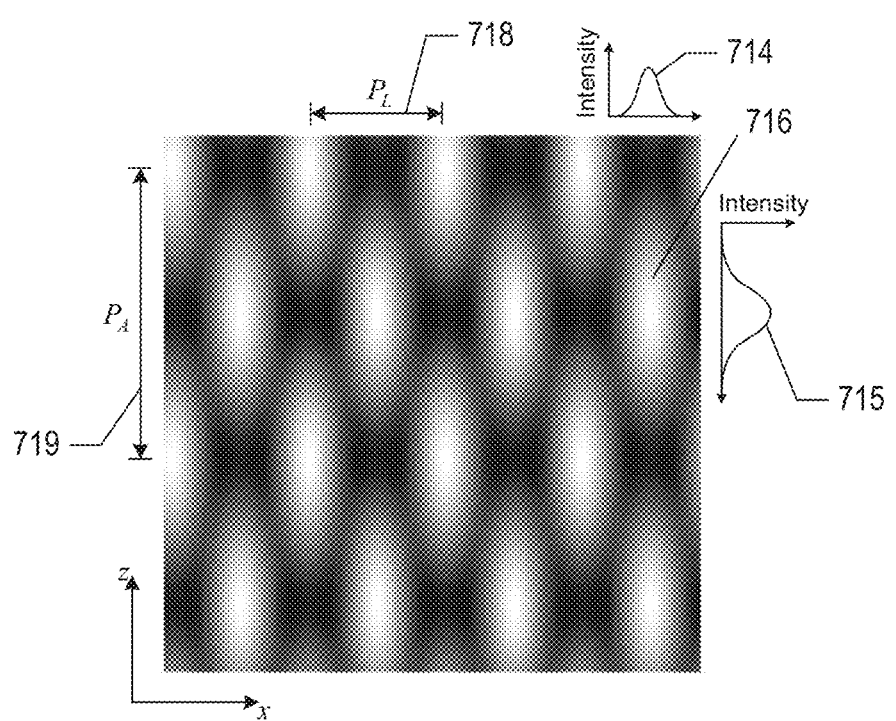
FIG. 7D shows an intensity distribution of a three-dimensional structured illumination pattern.
Figure 9A:
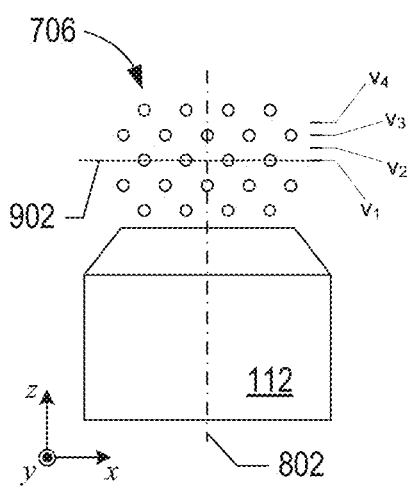
FIGS. 9A-9D show an example of a three-dimensional structured illumination pattern stepped parallel to an optical axial of an objective lens.
Figure 9B:
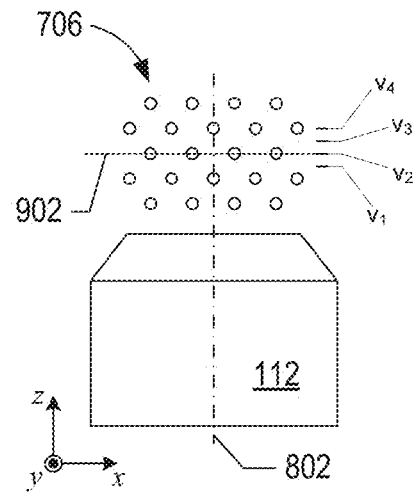
Figure 9C:
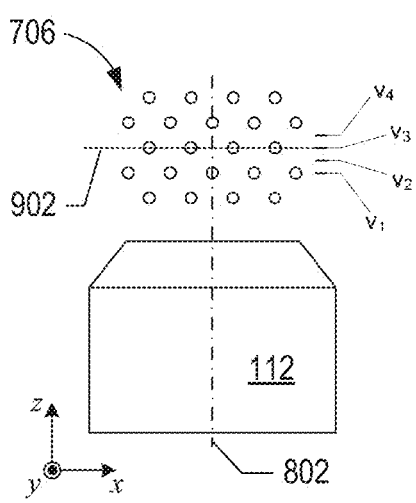
Figure 9D:
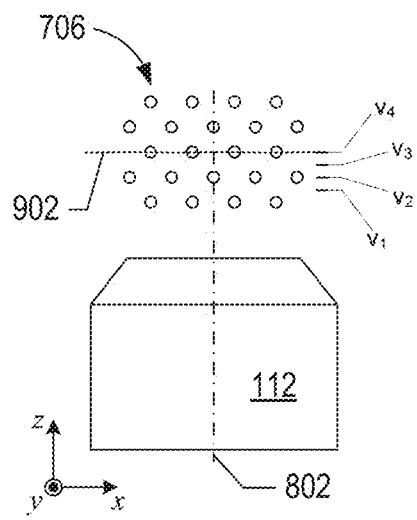

FIG. 7D shows an xz-plane, cross-sectional view of the intensity distributions of bright lines of excitation light comprising a 3D-SIP. The bright lines are represented by elongated white spots that fade to gray as the intensity decreases away from the centers of the lines. Gaussian curves 714 and 715 represent lateral (i.e., x-direction) and axial (i.e., z-direction) cross-sectional intensity distributions, respectively, across a bright line 716. Black or very dark regions between the bright lines represent destructive interference regions in which the excitation light intensity is very small or nonexistent. The lateral pitch, $P_l$, 718 and axial pitch, $P_a$, 719 are determined by the angle of the outer beams 124 and 126 with respect to the central beam 125. For example, a lateral pitch can be about 440 to 450 nm while the axial pitch is typically twice as long.

As described above with reference to FIG. 1, the sample 114 may include a number of different types of components, such as organelles of a cell, and each type of component may be labeled with a different type of fluorescent probe. Each type of probe is designed to bind specifically to a particular component of the sample, and each type of fluorophore is bound to a particular type of probe. When the sample 114 is illuminated with a 3D-SIP with an excitation frequency, each bright line of the 3D-SIP that intersects a fluorophore is likely to excite emission of light from the fluorophore. Fluorophores attached to components of the sample 114 that are located in the dark regions between the bright lines shown in FIG. 7D are less likely to fluoresce because the intensity of the excitation light is significantly lower, while Fluorophores that intersect the higher intensity regions of the bright lines are more likely to fluoresce. A portion of the fluorescent light emitted from fluorescing fluorophores is collected and collimated by the objective lens 112 into the beam 138, shown in FIG. 1, and is transmitted to the detector 142.

Image data is acquired by taking an image of the fluorescing fluorophores excited by the 3D-SIP, moving the 3D-SIP to a new position in the sample, followed by taking another image, and systematically repeating these steps to acquire of number of images. The IPC 130 can be used to laterally translate the 3D-SIP 706 perpendicular to the optical axis of the objective lens 112. FIGS. 8A-8E show an example of stepping the 3D-SIP 706 through five equally spaced lateral positions of a lateral pitch centered about an optical axis 802 of the objective lens 112. In the example of FIGS. 8A-8E, the bright lines of the 3D-SIP 706 extend in the y-direction, as described above with reference to FIG. 8. Marks labeled $h_1$-$h_5$ in FIGS. 8A-8E, represent five laterally spaced positions separated by approximately equal spatial intervals that are centered about the optical axis 802. In other words, the spacing between the bright lines of the 3D-SIP 706 is divided by six to generate finer spacing distances, with five lateral steps used to sample the finer-spacing distance. Dotted line 804 identifies the center of the 3D-SIP 706 in the z-direction. FIGS. 8A-8E represent five discrete lateral steps in which the 3D-SIP 706 is translated substantially perpendicular to the optical axis 802. For example, in FIG. 8A, the 3D-SIP 706 is in the first lateral position denoted by "$h_1$," and in FIG. 8B, the 3D-SIP 706 is stepped through an interval to the second lateral position denoted by "$h_2$." At each of the five lateral positions represented in FIGS. 8A-8E, an image of the excited light-emitting fluorophores is captured. The final step resets the 3D-SIP to the first lateral position for the next cycle.

The IPC 130 can also be used to axially translate the 3D-SIP 706 parallel to the optical axis of the objective lens 112. FIGS. 9A-9D show an example of the 3D-SIP 706 stepped through four equally spaced axial positions of an axial pitch. Marks labeled $v_1$-$v_4$ in FIGS. 9A-9D, represent four axial positions separated by approximately equal axial spatial intervals. In other words, the spacing between the bright lines of the 3D-SIP 706 is divided by five to generate a finer spacing distance, with four lateral steps used to sample the finer-spacing distance. In the example of FIG. 9, dotted line 902 passes through the center of the 3D-SIP 706 in the x-direction. FIGS. 9A-9D represent four discrete steps in which the 3D-SIP 706 is axially translated substantially parallel to the optical axis 802. For example, in FIG. 9A, the 3D-SIP 706 is in the first axial position denoted by "$v_1$," and in FIG. 9B, the 3D-SIP 706 is stepped through an axial interval to the second axial position denoted by "$v_2$." At each of the four axial positions represented in FIGS. 9A-9D, the 3D-SIP can be stepped through the five lateral positions represented in FIGS. 8A-8E with an image of the light-emitting fluorophores captured for each step for a total of 20 separate images. The final step resets the 3D-SIP to the first axial position for the next cycle.

The five lateral steps and four axial steps illustrated in FIGS. 8 and 9 merely represent examples of the number of lateral and axial steps a 3D-SIP can be stepped through. In practice, the number of lateral and axial steps can range from as few as one step to more than five steps, depending on how many spatial intervals the lateral and axial pitches are divided into. Note that depending on the position-decoding scheme, the steps need not be evenly spaced.

Figure 10:
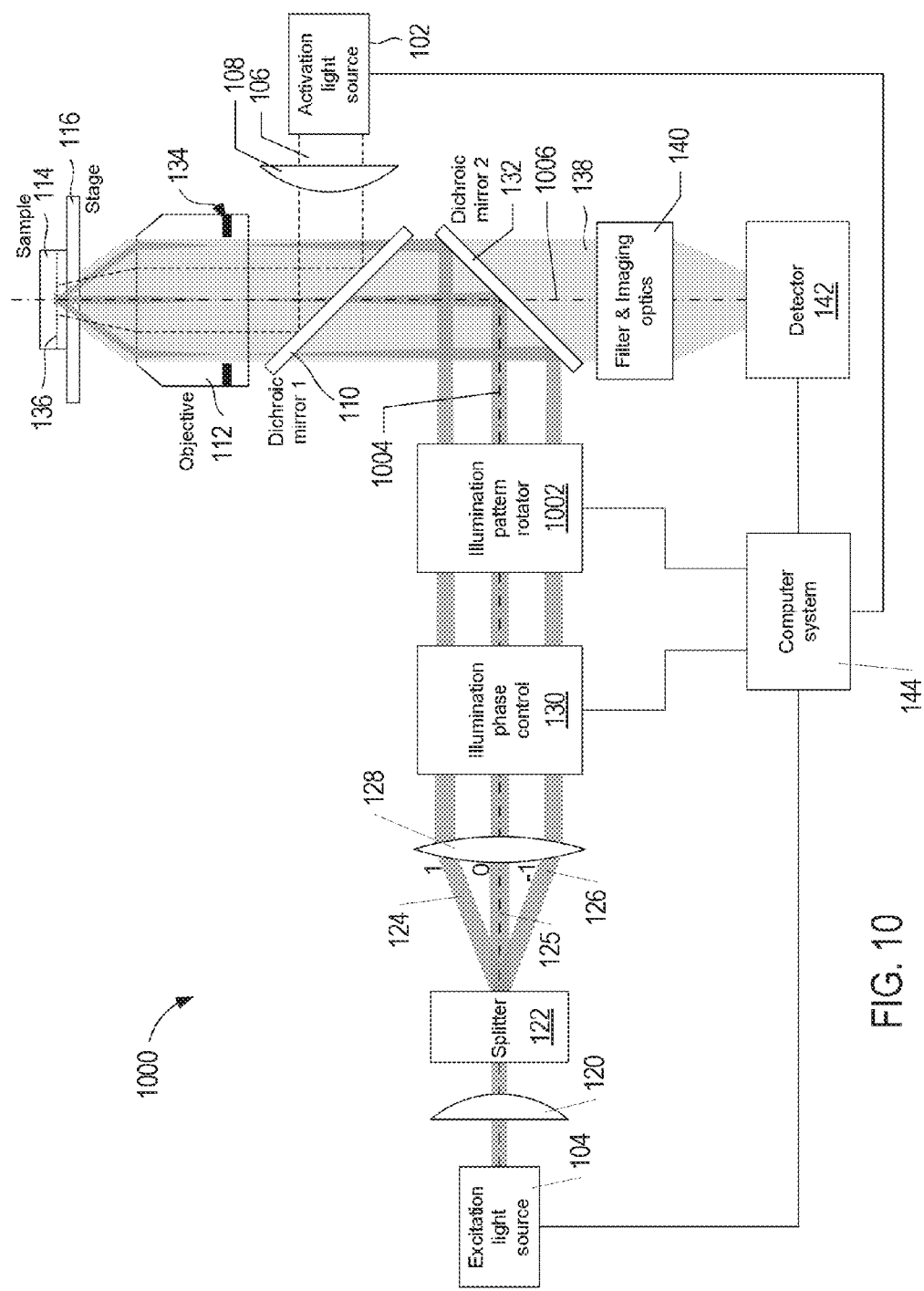
FIG. 10 shows a schematic representation of an example fluorescence microscope.

In other embodiments, a fluorescence microscope can include an illumination pattern rotator ("IPR") that rotates the 3D-SIP in the lateral plane (i.e., xy-plane) perpendicular to the optical axis of the objective lens. FIG. 10 shows a schematic representation of an example fluorescence microscope 1000. The microscope 1000 is similar to the microscope 100 except the microscope 1000 includes an IPR 1002 that intersects the beams 124-126 between the IPC 130 and the second dichroic mirror 132 and is electronically connected to, and operated by, the computer system 144. FIG. 10 includes two substantially perpendicular optical axes 1004 and 1006. The IPR 1002 rotates the beams 124-126 through an angle about the optical axis 1004, which, in turn, results in a rotation of the 3D-SIP in the sample 114 through the same angle about the optical axis 1006.

Figure 11A:
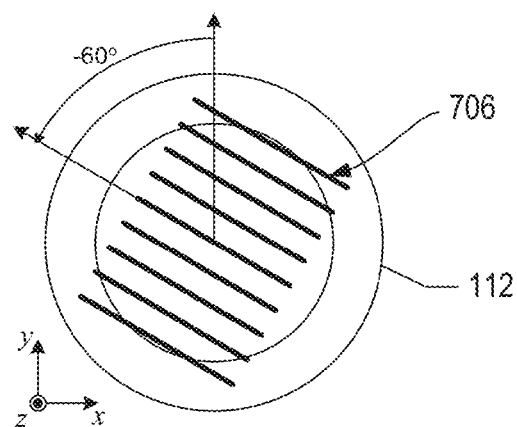
FIGS. 11A-11C show top views of three-dimensional structured illumination pattern formed above an objective lens and rotated through three rotation angles.
Figure 11B:
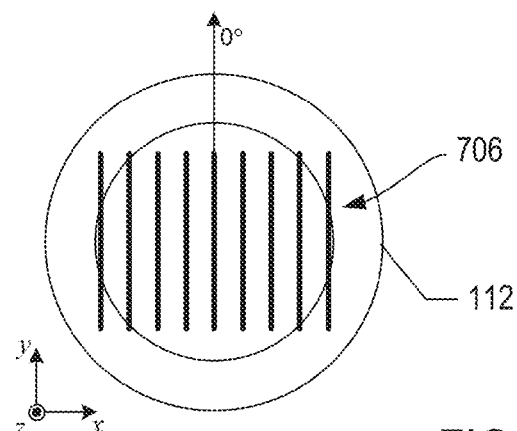
Figure 11C:
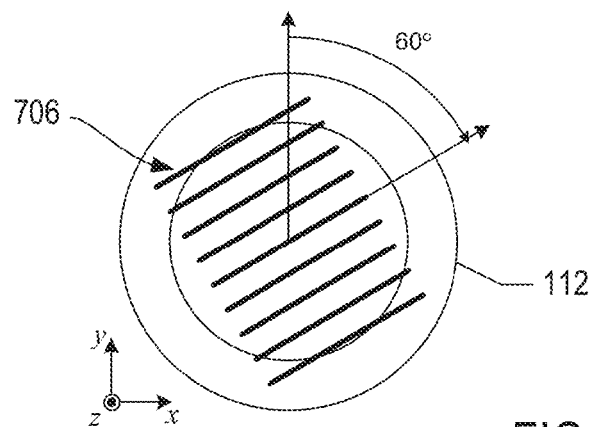

FIGS. 11A-11C show top views (i.e., xy-plane) of the 3D-SIP 706 formed above the objective lens 112 in the sample 114. In FIG. 11A, the IPR 1102 rotates the beams 124-126 about the optical axis 1104 so that the bright lines of the 3D-SIP 706 are initially at −60° with respect to the y-axis above the objective lens 112. In FIG. 11B, the IPR 1102 rotates the beams 124-126 through 60° about the optical axis 1004 which results in the 3D-SIP 706 being rotated through 60 degrees about the optical axis 1006 to angle of 0° with respect to the y-axis. In FIG. 11C, the IPR 1002 rotates the beams 124-126 through an additional 60 degrees about the optical axis 1004 which results in the 3D-SIP 706 being rotated through 60° about the optical axis 1006 to angle of 60° with respect to the y-axis.

Figure 12A:
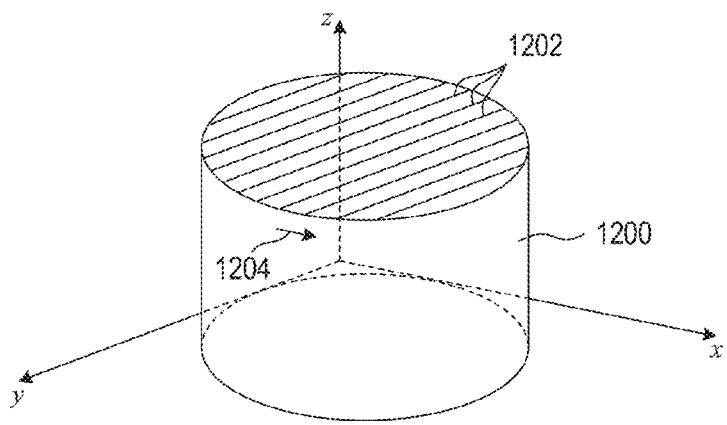
FIGS. 12A-12G show an example of image-data collection for imaging of a sample specimen represented by a cylindrical volume.
Figure 12B:
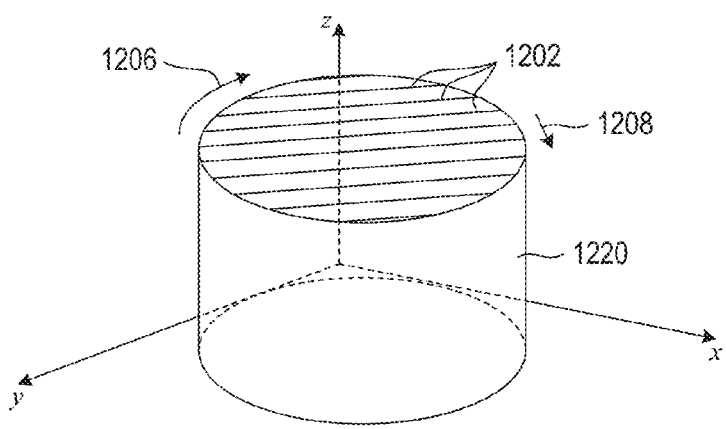
Figure 12C:
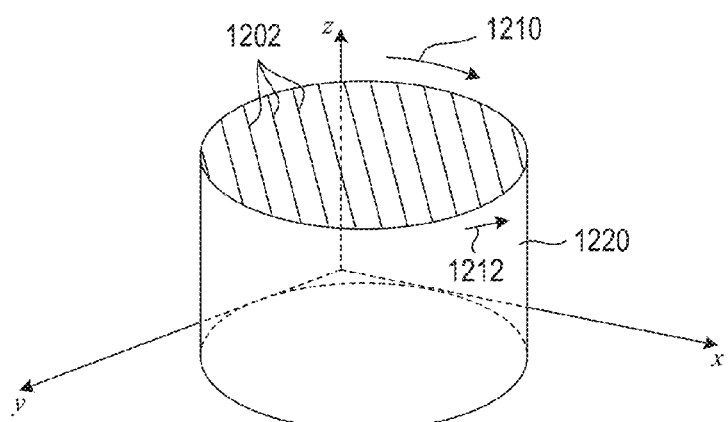
Figure 12D:
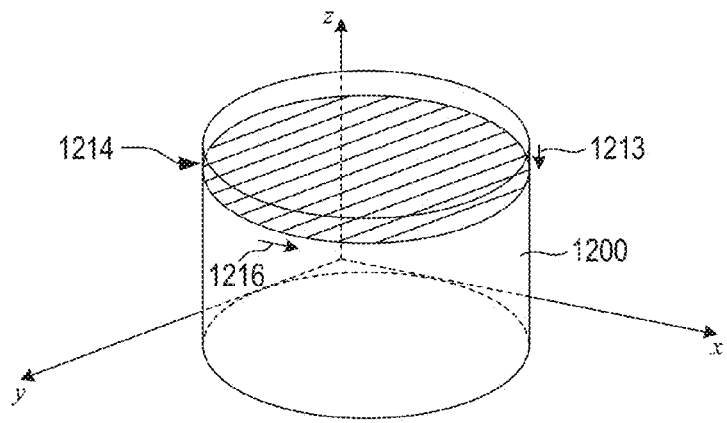
Figure 12E:
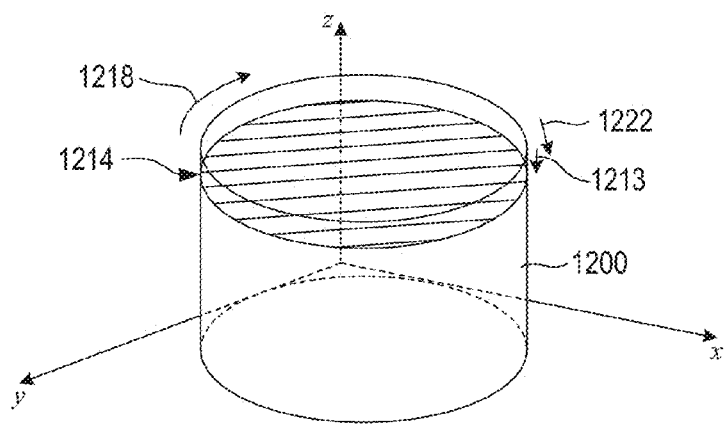
Figure 12F:
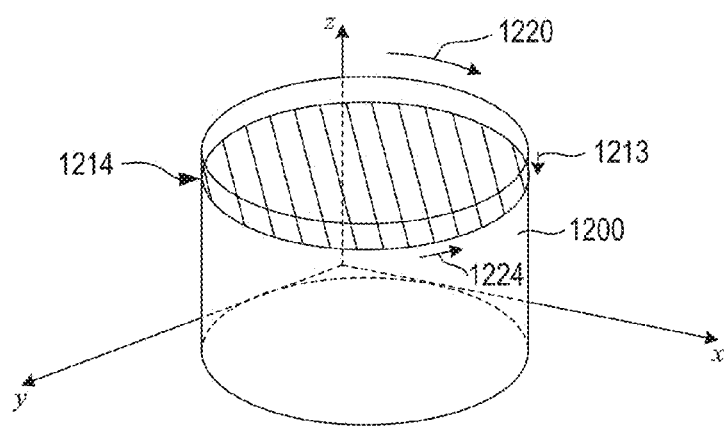
Figure 12G:
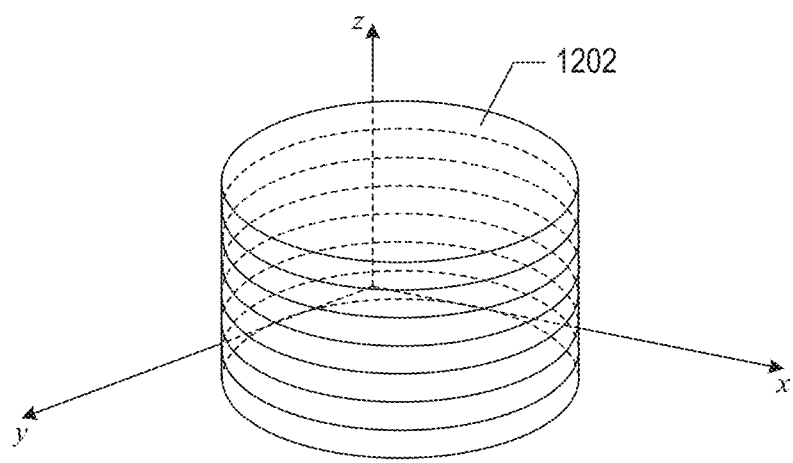

The IPC 130 and the IPR 1002 can be operated together to systematically scan a stochastically activated sample specimen with a 3D-SIP. FIGS. 12A-12G show an example of image-data collection for 3D-SIM imaging of a sample specimen represented by a cylindrical volume 1200. The objective lens (not shown) can be located below the xy-plane of the Cartesian coordinate system represented in FIG. 12. In FIGS. 12A-12G, parallel lines 1202 represent the angular positions of the bright lines of a 3D-SIP. As discussed above with reference to FIG. 8, beams are focused at a focal plane in or behind the objective lens causing the 3D-SIP to be formed in an object plane of the sample 1202. In order to reconstruct a higher-resolution image for the object plane, the mathematical technique for 3D-SIM data processing reconstructs the higher-resolution image for the sample plane from data collected from a sample volume represented by the cylinder 1200. First, as shown in FIG. 12A, the 3D-SIP is centered on the top surface, or a first plane, of the sample volume 1200 with the bright lines of the 3D-SIP oriented parallel to the y-axis and first image of fluorescing fluorophores is recorded. Then, as represented by directional arrow 1204, the 3D-SIP is stepped laterally through step through spatial intervals in a direction orthogonal to the lines 1202, and an image is recorded for each step. For example, five lateral steps can be carried out to produce five different, laterally shifted 3D-SIPs from which five separate images are collected, as described above with reference to FIG. 8. Then, as shown in FIG. 12B, the 3D-SIP is rotated by 60 degrees 1206 and a next image recorded. The 3D-SIP is then laterally stepped, as represented by direction arrow 1208, through a number of spatial intervals and an image is recorded for each step. Then, as shown in FIG. 12C, the 3D-SIP is rotated by another 60 degrees 1210 (i.e., 120 degrees or −60 degrees with respect to the original orientation of FIG. 12A), and the 3D-SIP is laterally stepped, as represented by directional arrow 1212, through a number of steps with an image recorded for each step. The angle of the 3D-SIP is reset to 0 degrees with respect to the y-axis and the 3D-SIP is then stepped axially 1213 (i.e., z-direction) by centering the 3D-SIP on a second plane 1214, as shown in FIG. 12D, and an image is captured for a number of lateral steps in a direction 1216 orthogonal to the lines 1202. FIGS. 12E and 12F represent a 60 degree rotation 1218 and an additional 60 degree rotation 1220 of the 3D-SIP and associated lateral steps in the directions 1222 and 1224, respectively, with the same number of lateral steps performed and images captured for each rotation angle. FIG. 12G shows eight regularly-spaced object planes spaced in the axial direction of the sample volume 1202 that are each sampled as described above with reference to FIGS. 12A-12F. For example, each of the eight planes can be illuminated with three rotations and five lateral steps for each rotation to generate a total of 120 different recorded images of the sample 1200.

In practice, the number of object planes or steps in the axial direction (i.e., z-direction) is not limited to eight and the number of steps in a lateral direction is not limited to five. In general, the number of recorded images of a sample volume can be $l \times n \times m$, where l is the number of angular rotations in each object plane of the sample volume, n is the number of lateral steps, and m is the number of axial steps. Note that the minimum number of rotations is not limited to three. 3D-SIP translations and rotations can be combined. In a well-calibrated system, as few as three images may be sufficient to super-resolve an ensemble of fluorophores.

Methods for Resolving Centroid Positions

Figure 13:
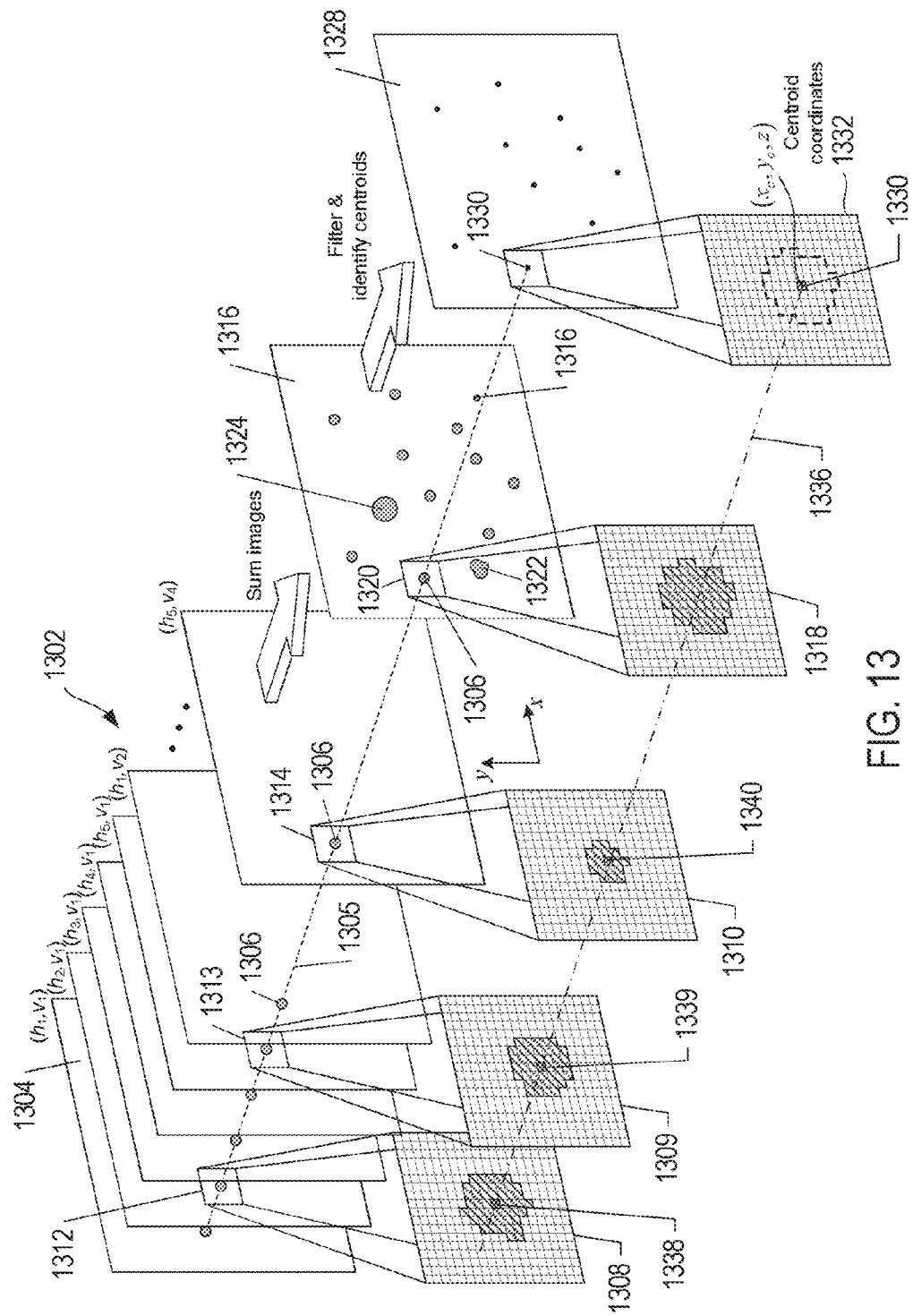
FIG. 13 shows a hypothetical series of images of a set of stochastically activated fluorophores of a sample specimen.

FIG. 13 shows a hypothetical series of images 1302 of a set of stochastically activated fluorophores of a sample specimen captured. In this example, the images are captured using a 3D-SIP as described above with reference to FIGS. 8 and 10. Each image is identified by the lateral and axial steps the 3D-SIP is in at the time the image is captured. For example, image 1304 is identified as $(h_1, v_1)$, which represents an image of the light-emitting fluorophores when the 3D-SIP is in lateral position $h_1$ and axial position $v_1$ described above with reference to FIGS. 8 and 10. Because each image is obtained by exciting the activated fluorophores with the 3D-SIP in a different position within the sample, the spot associated with each activated fluorophore in image is different. For example, a dashed line 1305 through each of the images 1302 identifies a spot 1306 common to the images 1302 and represents an image of a single light-emitting fluorophore excited by the 3D-SIP. FIG. 13 includes magnified views 1308-1310 of subregions 1312-1314 of the images $(h_3, v_1)$, $(h_5, v_1)$, and $(h_5, v_4)$, respectively, with image pixels represented by squares. The spot 1306 is represented in the magnified views 1308-1310 as a group of shaded pixels. Each pixel in the series of images 1302 has an (x, y) coordinate and an intensity, I. For the sake of convenience the pixels shown in magnified views 1308-1310 are represented by the same shading, but in practice, actual recorded pixel intensities are distributed according to an Airy disk, as described above with reference to FIGS. 3 and 4.

The images 1302 are summed to produce a summed image 1316 of the stochastically activated fluorophores of the sample. Each pixel intensity of the summed image 1316 can be calculated by summing the intensities of corresponding pixels in the images 1302:

$$I(x_i, y_i) = \sum_{j=1}^{M} I_j(x_i, y_i)$$

where $(x_i, y_i)$ are pixel coordinates, M is the number of images in a series of images, and j is the image index. Shaded pixels in magnified view 1318 of a region 1320 represent the sum of the intensities of corresponding pixels in the spot 1306 in each of the images 1302. After the summed image 1316 has been acquired, the summed image 1306 is filtered by examining the size and shape of the individual spots. Irregularly shaped spots, such as spot 1322, and spots with diameters that are greater than a maximum diameter threshold or less than a minimum diameter threshold, such as spots 1324 and 1326, respectively, are discarded from the summed image 1316 and the images 1302.

Next, the centroid coordinates $(x_c, y_c)$ the remaining spots in the summed image 1316 are calculated to generate a filtered image of the centroids 1328. For example, the centroid $(x_c, y_c)$ of each spot can be calculated using weighted averages:

$$x_c = \frac{1}{N}\sum_{i=1}^{N} I_i x_i$$

$$y_c = \frac{1}{N}\sum_{i=1}^{N} I_i y_i$$

where N represents the number of pixels identified as belonging to a spot, and $I_i$ represents the intensity of the pixel with coordinates $(x_i, y_i)$. The z-coordinate is determined by the magnification setting of the microscope. Alternatively, the centroid can be calculated using unweighted averages (i.e., the intensities $I_i$ are assigned the value "1"). In still other embodiments, centroids can be calculated by fitting a Gaussian distribution to each spot with the pixel coordinates corresponding to the Gaussian maximum identified as the centroid of the spot. In FIG. 13, shaded pixel 1330 in magnified view 1332 of the filtered image 1328 represents the centroid pixel of the spot 1306 in the summed image 1316.

Next, the centroids in the filtered image 1328 are used as the centroids of the corresponding spots in the images 1302. For example, dot-dashed line 1336 passes through the centroid pixel 1330 and through shaded pixels 1338-1340. The shaded pixels 1338-1340 have the same coordinates as the centroid 1330 and are designated as the centroids of the spot 1306 in magnified views 1308-1310, respectively.

Figure 14:
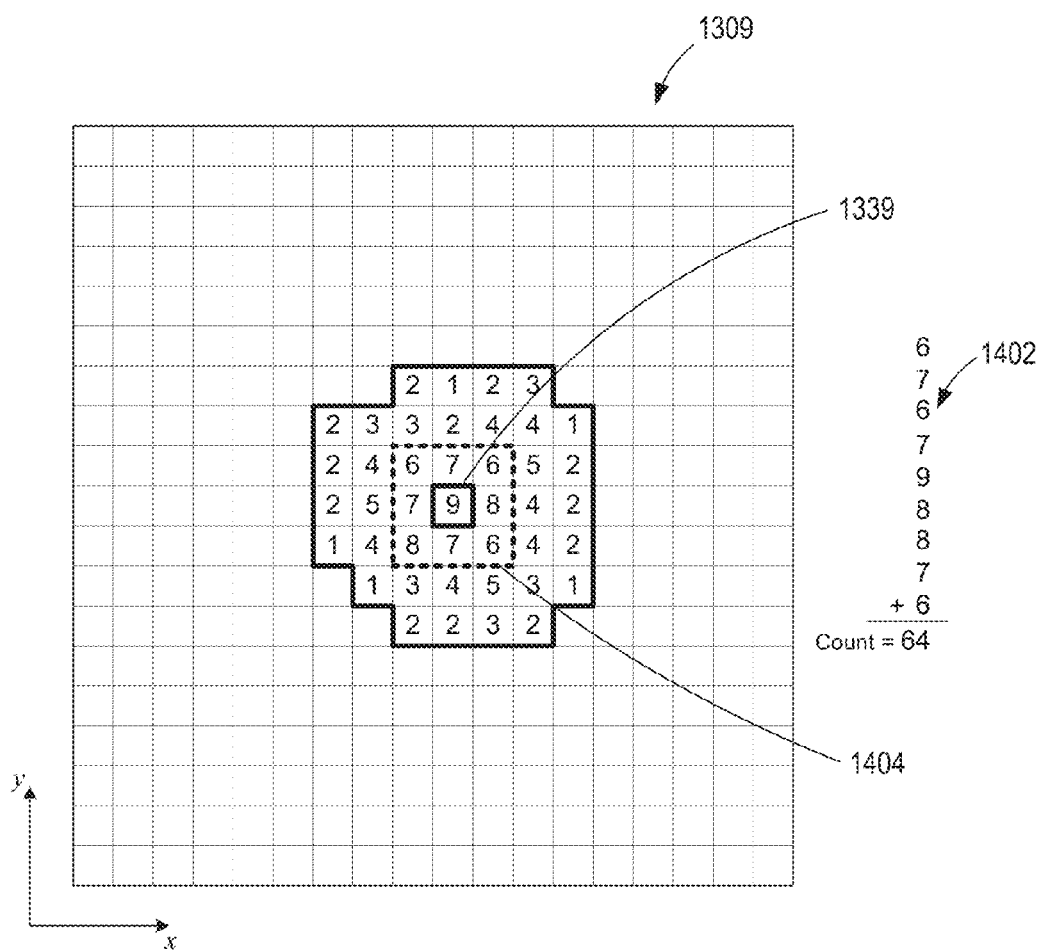
FIG. 14 shows an enlargement of a spot represented in a magnified view of FIG. 13.

Next, a count is calculated for each of the filtered spots in the images 1302. The count is the sum of the intensities of the pixels that are within a neighborhood of the centroid of a spot. FIG. 14 shows an enlargement of the spot represented in the magnified view 1309 of FIG. 13. The intensities of the pixels comprising the spot are represented by integer values. For example, the intensity of the centroid pixel 1339 is "9." Note the coordinates of the pixel 1339 are the same as the coordinates of the centroid pixel 1330 shown in FIG. 13. In this example, the count assigned to the pixel 1339 is "64," which is determined by summing 1402 the intensities of the pixels that are within a 3×3 neighborhood of pixels, identified by dashed-line square 1404, centered about the centroid pixel 1339. In other embodiments, the neighborhood can be a 5×5 neighborhood centered about the centroid pixel. In still other embodiments, the neighborhood can include weighting factors multiplied by each of the pixel intensities that fall within the neighborhood.

After counts have been assigned to the centroids of the spots in the images 1302, the counts are used to resolve and refine the centroid coordinates of the filtered image 1318 to generate a resolved image. In one embodiment, this can be accomplished by generating count vectors whose elements are the counts associated with spots common to each of the images 1302 and mathematically combining the count vectors with cosine and sine vectors that represent the variation in the intensity of the bright lines of the 3D-SIP as the pattern is stepped through the sample volume. The lateral and axial count vectors can be represented by:

$$\langle \text{count} \rangle_L = \langle D_{s,h,v} \rangle$$

$$\langle \text{count} \rangle_A = \langle D_{s,h,v} \rangle$$

where $D_{s,h,v}$ are vector elements that represent the count of a spot, with spot index s, and h and v are indices that identify the image in the series of images. The interactions between a fluorophore and the bright lines of a 3D-SIP can be characterized by sine and cosine functions with periods of full oscillation within the lateral and axial pitches $P_L$ and $P_A$, respectively. Cosine and sine lateral vectors are represented by:

$$\langle \cos \rangle_L = \left\langle \cos\left(\frac{j2\pi}{n}\right) \right\rangle$$

$$\langle \sin \rangle_L = \left\langle \sin\left(\frac{j2\pi}{n}\right) \right\rangle$$

where $\cos(j2\pi/n)$ are cosine vector elements and $\sin(j2\pi/n)$ are sine vector elements with n equal to the number of steps in the lateral direction, and j is a step index that ranges from 0 to n−1. Cosine and sine lateral vectors are constructed for the axial directions as follows:

$$\langle \cos \rangle_A = \left\langle \cos\left(\frac{j2\pi}{m}\right) \right\rangle$$

$$\langle \sin \rangle_A = \left\langle \sin\left(\frac{j2\pi}{m}\right) \right\rangle$$

where $\cos(j2\pi/m)$ are cosine vector elements and $\sin(j2\pi/m)$ are sine vector elements with m equal to the number of steps in the axial direction from 0 to m−1. For each spot, the corresponding lateral count vector is combined with associated lateral cosine and sine vectors to compute a lateral phase given by:

$$\phi_L = \tan^{-1}\left(\frac{\langle \cos \rangle_L \cdot \langle \text{count} \rangle_L}{\langle \sin \rangle_L \cdot \langle \text{count} \rangle_L}\right)$$

where "•" is the scalar or dot product. And for each spot the axial count vector is combined with the axial cosine and sine vectors to compute an axial phase given by:

$$\phi_A = \tan^{-1}\left(\frac{\langle \cos \rangle_A \cdot \langle \text{count} \rangle_A}{\langle \sin \rangle_A \cdot \langle \text{count} \rangle_A}\right)$$

The phases $\phi_L$ and $\phi_A$ are converted to lengths and used to resolve the centroid coordinate of the spot.

An example of using cosine, sine and count vectors to resolve a centroid coordinates of a spot in a filtered image is now described with reference to FIGS. 15-17. FIG. 15 shows an xz-plane, cross-sectional view of four lines of a 3D-SIP, each line represented by a different line pattern, stepped through the lateral and axial spatial intervals described above with reference to FIGS. 8 and 9. Ovals are used to represent the xz-plane cross-sectional shape of the intensity distribution of the bright lines of excitation light in the 3D-SIP, described above with reference to FIG. 7D. For example, solid ovals, such as solid oval 1502, represent the xz-plane cross-section of the same line stepped through the lateral and axial positions described above with reference to FIGS. 8 and 9. Shaded circle 1504 represents a fluorophore of a sample, which interacts with the line 1502 as the line 1502 is stepped through the lateral and axial positions. As the line is stepped closer and eventually envelops the fluorophore 1504, the intensity of the light emitted from the fluorophore increases. For example, when the line 1502 is in axial position $v_3$, the intensity of the light emitted from the fluorophore increases and then decreases as the line 1502 is stepped through lateral positions $h_1$-$h_5$.

Figure 15B:
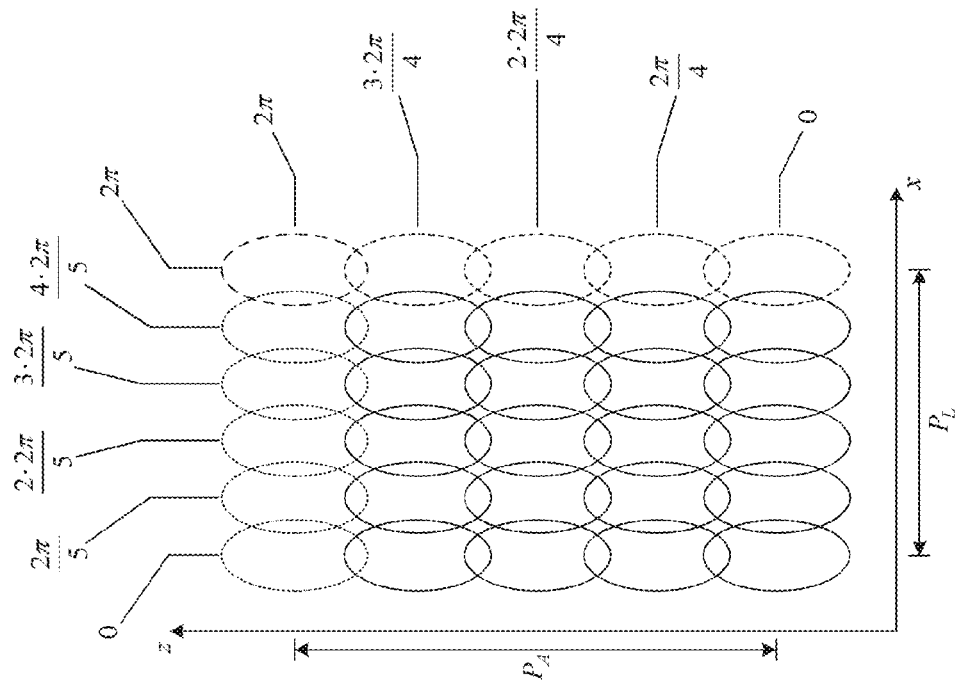
FIGS. 15A-15B shows a cross-sectional view of a three-dimensional structured illumination pattern stepped through lateral and axial spatial intervals.
Figure 15A:
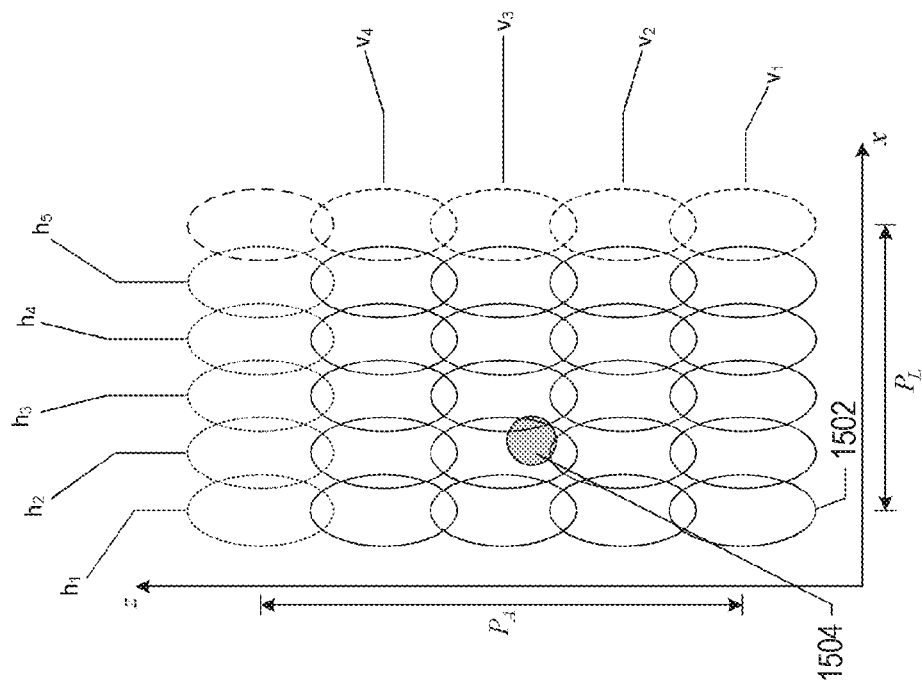

Although the fluorophore 1504 has at least some degree of overlap with the excitation light of the line 1502 as the line 1502 is stepped through the lateral and axial positions illustrated in FIG. 15A, the strongest interactions occur when the line 1502 is stepped through the lateral positions $h_1$-$h_5$ and the axial position is $v_3$ and when the lateral position is $h_2$ and the line is stepped through the axial positions $v_1$-$v_4$. As a result, the images associated with these positions are selected to resolve the x- and z-coordinates of the fluorophore 1504. In other words, the counts associated with the spot that represents the fluorophore 1504 in each of the images $(h_1, v_3)$, $(h_2, v_3)$, $(h_3, v_3)$, $(h_4, v_3)$, and $(h_5, v_3)$ are used to form a lateral count vector represented by:

$$\langle \text{count} \rangle_L = \langle D_{s,1,3}, D_{s,2,3}, D_{s,3,3}, D_{s,4,3}, D_{s,5,3} \rangle$$

and the counts associated with the same spot that represents the fluorophore in each of the images $(h_2, v_1)$, $(h_2, v_2)$, $(h_2, v_3)$, and $(h_2, v_4)$ are used to form an axial count vector represented by:

$$\langle \text{count} \rangle_A = \langle D_{s,2,1}, D_{s,2,2}, D_{s,3,2}, D_{s,4,2} \rangle$$

As described above with reference to FIG. 15A, the interaction between the fluorophore 1504 and the line 1502 sinusoidally increases and decreases as the line is stepped lateral through the positions $(h_1, v_3)$, $(h_2, v_3)$, $(h_3, v_3)$, $(h_4, v_3)$, and $(h_5, v_3)$ and sinusoidally increases and decreases as the line is stepped axially through the positions $(h_2, v_1)$, $(h_2, v_2)$, $(h_2, v_3)$, and $(h_2, v_4)$. These sinusoidal interactions can be characterized by sine and cosine functions with periods of full oscillation that are equal to the lateral and axial pitches $P_L$ and $P_A$ represented in FIG. 15A. In other words, the lateral and axial pitches $P_L$ and $P_A$ correspond to $2\pi$ radians and the intervals into which the pitches are divided can be represented in radians as shown in FIG. 15B. In particular, the axial positions $v_1$, $v_2$, $v_3$, and $v_4$ represented in FIG. 15A correspond to $0$, $\pi/2$, $\pi/2$, and $3\pi/2$ in FIG. 15B, respectively, and the lateral positions $h_1$, $h_2$, $h_3$, $h_4$, and $h_5$ represented in FIG. 15A correspond to $0$, $2\pi/5$, $4\pi/5$, $6\pi/5$, and $8\pi/5$, respectively, in FIG. 15B.

Figure 16A:
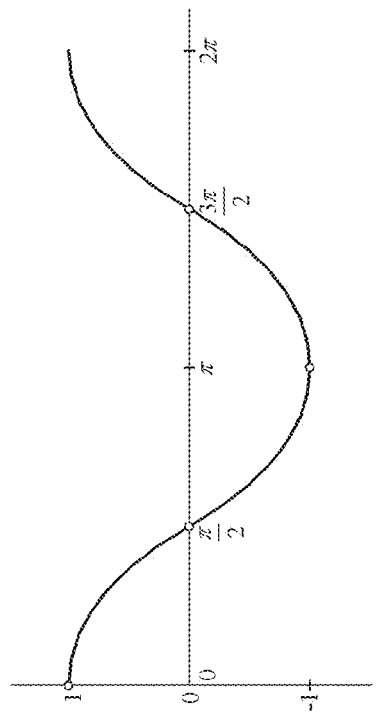
FIGS. 16A-16B show plots of cosine and sine curves, respectively, that characterize oscillations in lateral intensity variation encountered by a fluorophore.
Figure 16B:
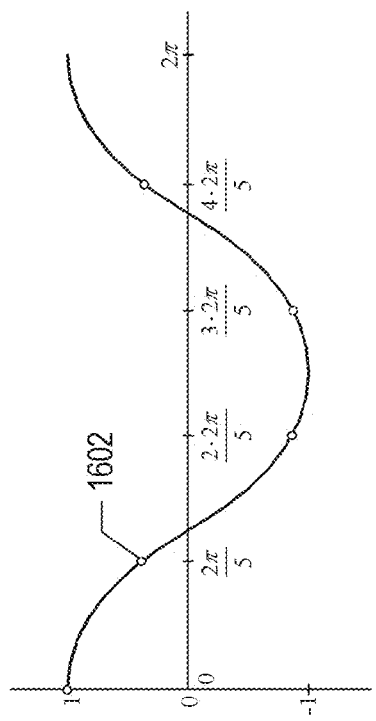

FIGS. 16A-16B show plots of cosine and sine curves, respectively, that characterize the oscillations in the intensity of the bright line 1502 encountered by the fluorophore 1504 as the line 1502 is stepped through the lateral positions $h_1$, $h_2$, $h_3$, $h_4$, and $h_5$. Open circles, such as open circle 1702 in FIG. 16A, represent cosine function values at $0$, $2\pi/5$, $4\pi/5$, $6\pi/5$, and $8\pi/5$, which are used to form a lateral cosine vector given by:

$$\langle \cos \rangle_L = \left\{ 1, \cos\left(\frac{2\pi}{5}\right), \cos\left(\frac{4\pi}{5}\right), \cos\left(\frac{6\pi}{5}\right), \cos\left(\frac{8\pi}{5}\right) \right\}$$

Figure 17A:
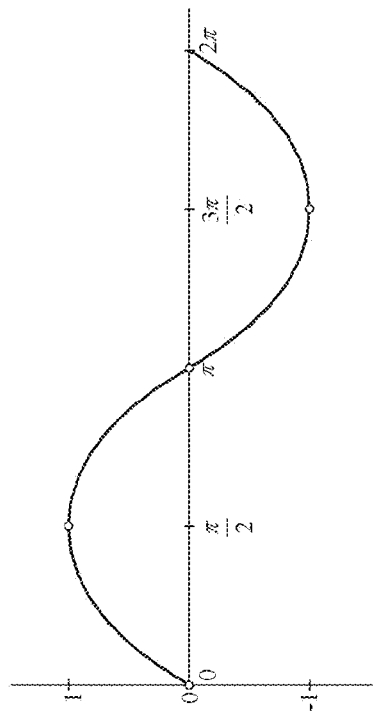
FIGS. 17A-17B show plots of cosine and sine curves, respectively, that characterize oscillations in axial intensity variation encountered by a fluorophore.
Figure 17B:
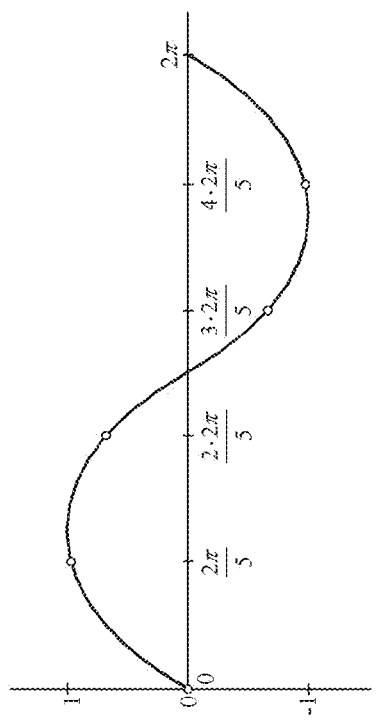

Likewise, open circles in FIG. 17B represent sine function values for the same positions are used to form a lateral sine vector given by:

$$\langle \sin \rangle_L = \left\{ 0, \sin\left(\frac{2\pi}{5}\right), \sin\left(\frac{4\pi}{5}\right), \sin\left(\frac{6\pi}{5}\right), \sin\left(\frac{8\pi}{5}\right) \right\}$$

FIGS. 17A-17B show plots of cosine and sine curves, respectively, that characterize the oscillations in the intensity of the bright line 1502 encountered by the fluorophore 1504 as the line 1502 is stepped through the axial positions $v_1$, $v_2$, $v_3$, and $v_4$. Open circles in FIG. 17A represent the cosine function values at $0$, $\pi/2$, $\pi$, and $3\pi/2$, which are used to form an axial cosine vector given by:

$$\langle \cos \rangle_A = \left\{ 1, \cos\left(\frac{\pi}{2}\right), \cos(\pi), \cos\left(\frac{3\pi}{2}\right) \right\}$$

Likewise, open circles in FIG. 17B represent the sine function values at the same positions and are used to from an axial sine vector given by:

$$\langle \sin \rangle_A = \left\{ 0, \sin\left(\frac{\pi}{2}\right), \sin(\pi), \sin\left(\frac{3\pi}{2}\right) \right\}$$

The lateral cosine and sine vectors are combined with the corresponding lateral count vector to compute a lateral phase given by:

$$\phi_L = \tan^{-1}\left(\frac{\langle \cos \rangle_L \cdot \langle \text{count} \rangle_L}{\langle \sin \rangle_L \cdot \langle \text{count} \rangle_L}\right)$$

$$= \tan^{-1}\left(\frac{\sum_{j=0}^{4} D_{s,j,3} \cos(j2\pi/5)}{\sum_{j=0}^{4} D_{s,j,3} \sin(j2\pi/5)}\right)$$

where "·" is the scalar or dot product. The axial cosine and sine vectors are combined with the corresponding axial count vector to compute an axial phase given by:

$$\phi_A = \tan^{-1}\left(\frac{\langle \cos \rangle_A \cdot \langle \text{count} \rangle_A}{\langle \sin \rangle_A \cdot \langle \text{count} \rangle_A}\right)$$

$$= \tan^{-1}\left(\frac{\sum_{j=0}^{3} D_{s,2,j} \cos(j2\pi/4)}{\sum_{j=0}^{3} D_{s,2,j} \sin(j2\pi/4)}\right)$$

The phases $\phi_L$ and $\phi_A$ can be converted from radians to length dimensions by:

$$x_t = \phi_L\left(\frac{P_L}{2\pi}\right)$$

$$z_t = \phi_A\left(\frac{P_A}{2\pi}\right)$$

which are used to compute resolved coordinates for the fluorophore as follows:

$(x_c+x_t,y_c,z+z_t)$

The method described above is repeated for each of centroids in the filtered image 1328 to produce a resolved image of the set of activated fluorophores.

The number of axial and lateral steps is not limited to those described above. In practice, any suitable number of steps can be used for each angle. For example, in order to move the SIP four steps for each rotational angle of the SIP, offset pitches of $P_L/4$ and $P_A/4$ can be used.

Figure 18:
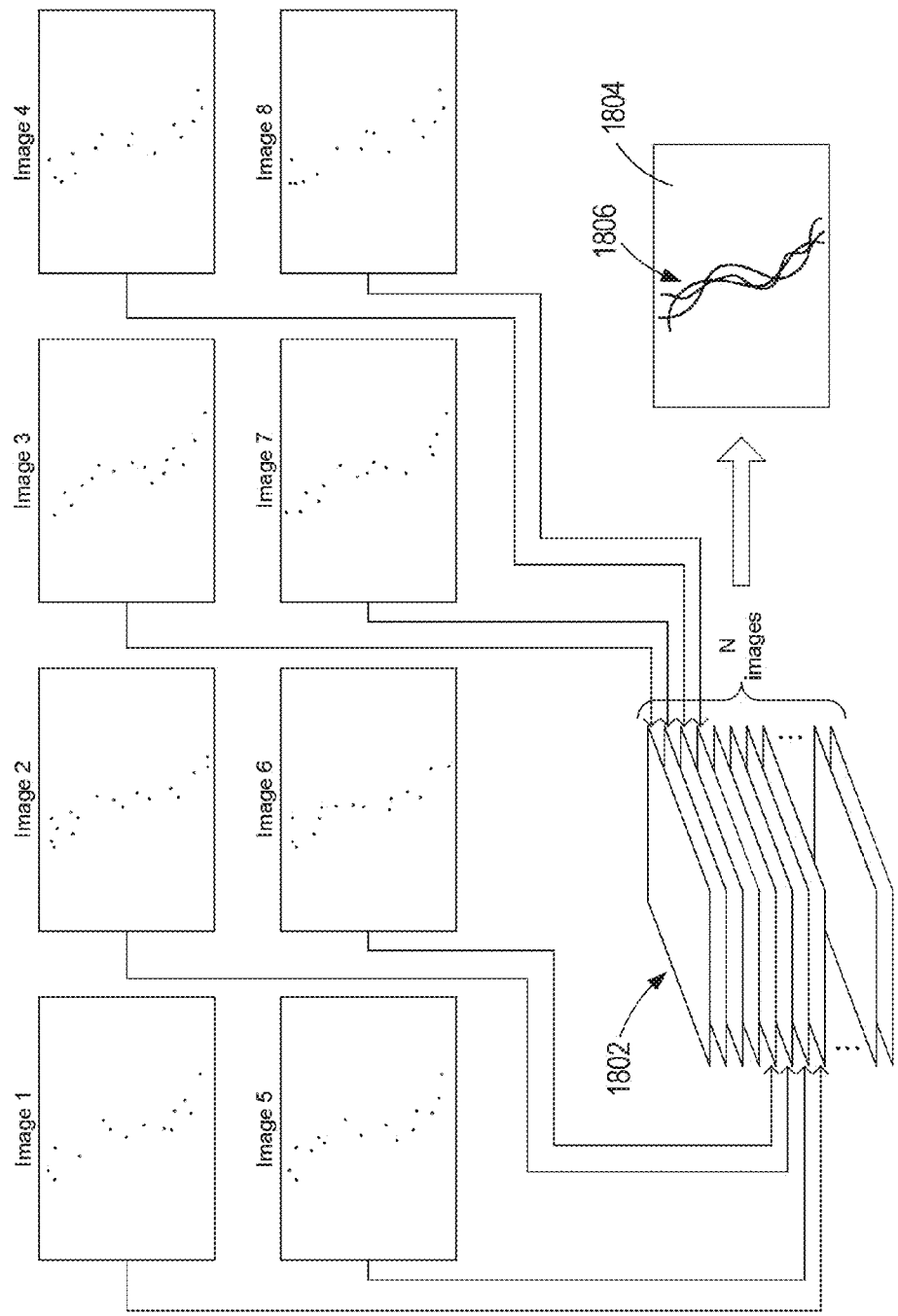
FIG. 18 shows an example of combining resolved images to obtain a super-resolution image.

The computational method described above to generate a resolved image is repeated to produce a set of resolved images, each of which is of a different set of activated fluorophores. The resolved images are then combined to form a super-resolution image of the sample. FIG. 18 shows an example of combining resolved images to obtain a super-resolution image of a sample. As shown in FIG. 18, for example, each of resolved images 1-8 are produced by collecting data from a different set of sparsely activated fluorophores, as described above with reference to FIGS. 13-17. The resolved images are then summed together 1802 to produce a final, composite super-resolution image 1804 that reveals a fluorophore-labeled structure, organelle, cellular component, or other feature 1806 in the sample.

The computational method described above may produce ambiguous axial phase $\phi_A$ positions for a fluorophore which can be address as follows. For example, suppose the axial phase position $\phi_A$ measurement is 21 degrees and 201 degrees, which are angles that are out of phase by 180 degrees or π radians and is referred to as a π-phase ambiguity. The π-phase ambiguities can be treated in the relative fluorophore-to-fluorophore coordinates or in absolute coordinates. Consider first the relative coordinates. In practice, the lateral pitch is typically of several hundred nanometers. For example, the lateral pitch can be 440 nm. As a result, the phase of the lateral pitch is approximately the same in bands separated by approximately 440 nm normal to the bright lines across the microscope field of view, which gives the fluorophore-to-fluorophore relative distances in these bands. A similar relationship exists for bands at η×440+220, which are 180 degrees out of phase with the first set of bands. In general, multiple lateral steps can be taken in more than one direction in the xy-plane. Multiple image of many fluorophores allowed for convergence on a self-consistent map of the fluorophores.

The π-phase ambiguity can also be resolved by mapping the 3D-SIP in x, y, and z-directions with respect to the microscope coordinates for each lateral and axial step of the 3D-SIP. The mechanism for moving the 3D-SIP is stable, and the 3D-SIP location can be known with high precision. The xy-plane centroid of each spot can be calculated with adequate resolution, and given the fluorophore position, the π-phase ambiguity is resolved.

For 2π-phase ambiguities (i.e., modulo 2π), the 3D-SIP repeats axially on a length scale similar to, but longer than, the lateral pitch. One approach to resolving the 2π-phase ambiguities is to map the fluorophores axially by changing the focus and observing the change in spot size and intensity with a different z-coordinate that corresponds to the focus.

Another approach is to change the pitch of the 3D-SIP and observe the induced change in the relative phase of the locations of the fluorophore ensemble. Fluorophores further above and below an arbitrary reference plane accumulate more phase shift, and the 2π-phase ambiguities can be resolved, provided the change in pitch is small enough that new 2π-phase ambiguities do not arise in a finite z-depth (e.g., 2 micrometers). The pitch of the 3D-SIP (lateral and axial) is governed by the separation of the two phase coherent outer beams 124 and 126 described above with reference to FIGS. 1 and 7, at the back of the objective lens 112. The IPC 130 can produce small changes in the phase of the outer beams 124 and 126 that result in pitch changes in the 3D-SIP. Note that changing the pitch in this manner can also be used to resolve the π-phase ambiguities described above and resolve lateral positioning. A small number of images at the new pitch can be used to resolve the 2π-phase ambiguities.

Figure 19:
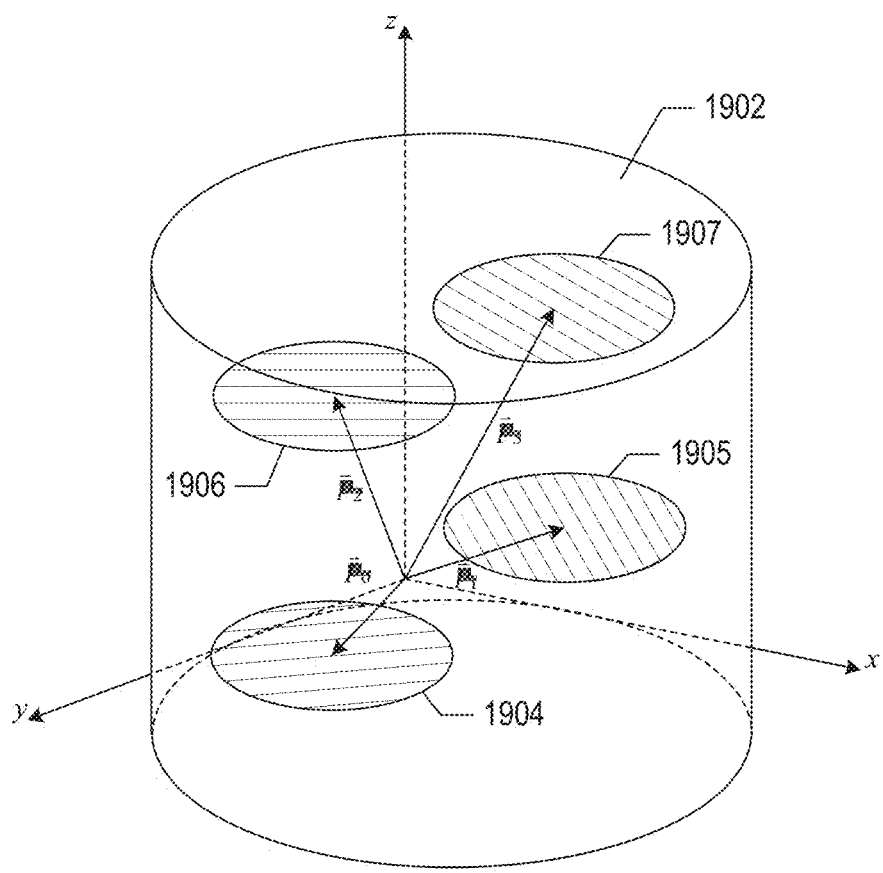
FIG. 19 shows an example representation of a three-dimensional structured illumination pattern rotated and shifted to different locations within a sample specimen.

In other embodiments, centroid coordinates of spots represented in a filtered image can be resolved using vectors that correspond to the position of the 3D-SIP within a sample volume. FIG. 19 shows an example representation of a 3D-SIP rotated and shifted to different locations within a sample specimen represented by a cylinder volume 1902. In FIG. 19, disks 1904-1907 represent four locations and orientations of the 3D-SIP within the sample 1902. The lines within each disk represent the direction along which the bright lines of excitation light of the 3D-SIP extend parallel to the xy-plane. The vectors $\vec{p}_0$, $\vec{p}_1$, $\vec{p}_2$, and $\vec{p}_3$ point to the approximate center of the 3D-SIP and represent four coordinate locations of the 3D-SIP centers with respect to a microscope Cartesian coordinate system.

Figure 20:
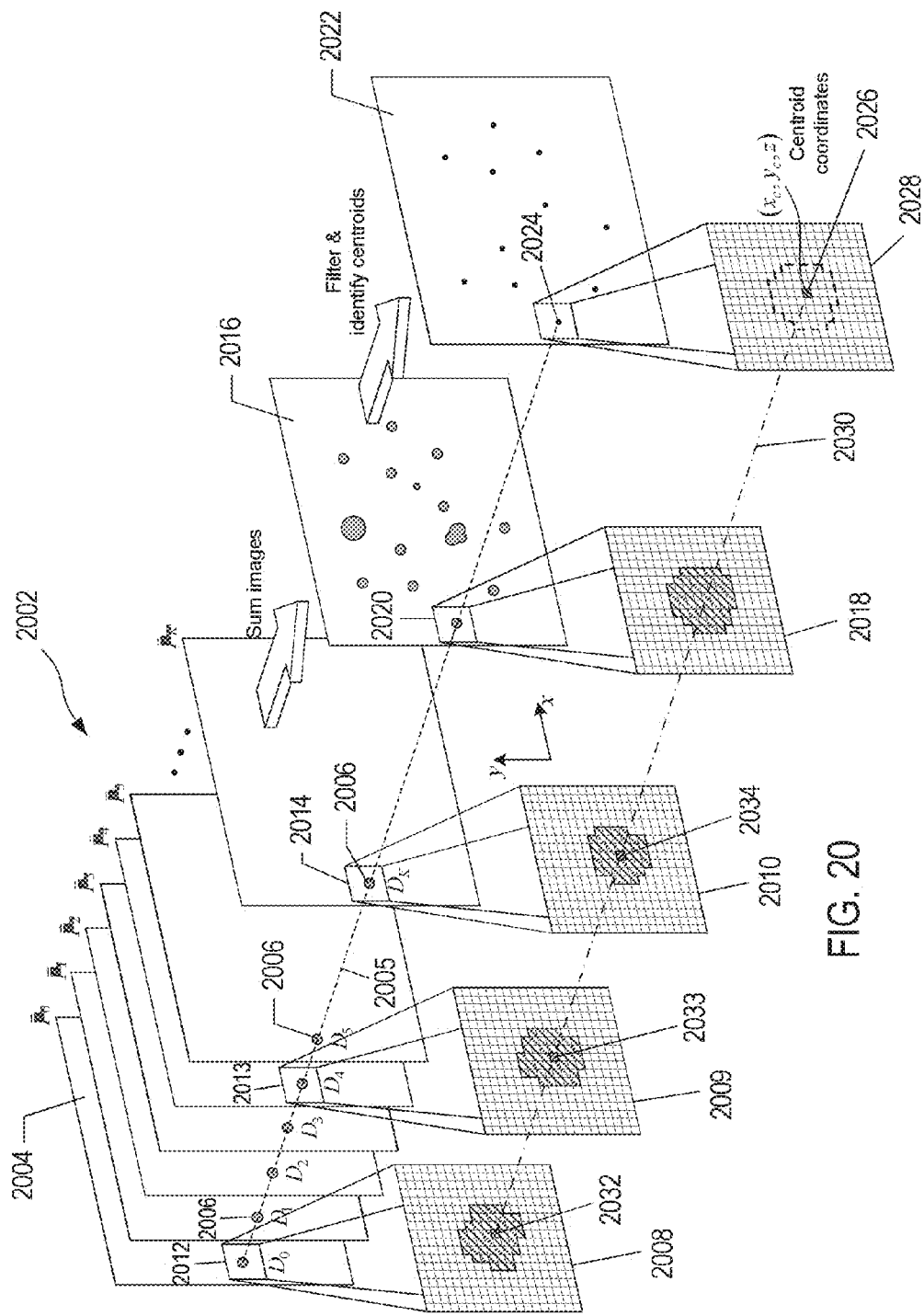
FIG. 20 shows a hypothetical series of images of a set of stochastically activated fluorophores of a sample specimen.

FIG. 20 shows a hypothetical series of images 2002 of a set of stochastically activated fluorophores of a sample specimen. In this example, the images are captured using a 3D-SIP that is moved within the volume of the sample as described above with reference to FIG. 19. Each image is identified by the vector that represents the approximate coordinate location of the center of the 3D-SIP. For example, image 2004 is identified as $\vec{p}_0$, which represents an image of the light-emitting fluorophores that is captured when the center of the 3D-SIP is located at $\vec{p}_0$ in the sample volume. Because each image is obtained by exciting the activated fluorophores with the 3D-SIP in a different position within the sample, the spots associated with each activated fluorophore are different in each of the images 2002. For example, a dashed line 2005 passes through a spot 2006 that is common to all of the images 2002. The spot in each of images 2002 represents the image of a single light-emitting fluorophore that is excited to some degree by the 3D-SIP when the center of the 3D-SIP is moved to the coordinate positions represented by the vectors $\vec{p}_0, \ldots \vec{p}_K$. FIG. 20 includes magnified views 2008-2010 of subregions 2012-2014 of the images $\vec{p}_0$, $\vec{p}_4$, and $\vec{p}_K$, respectively. The spot 2006 is represented in the magnified views 2008-2010 as a group of uniformly shaded pixels.

As described above with reference to FIG. 13, the images 2002 are summed to generate a summed image 2016. Shaded pixels in magnified view 2018 of a region 2020 represent the sum of the intensities of corresponding pixels associated with the spot 2006 in each of the images 2002. After the summed image 2016 is acquired, the spots are filtered according to the size and shape of the individual spots, as described above with reference to FIG. 13, and the centroid coordinates of the remaining spots are calculated to generate a filtered image of the centroids 2022, as described above with reference to FIG. 14. For example, dot 2024 in the filtered image 2022 represents the centroid of the spot 2006 common to each of the images 2002 as indicated by dotted line 2005, and is represented by a shaded pixel 2026 in magnified view 2028. The centroids of the spots in the filtered image 2022 are used as the centroids of the corresponding spots in each of the images 2002. For example, dot-dashed line 2030 passes through centroid pixel 2026 in magnified 2028 view and through shaded pixels 2032-2034. The shaded pixels 2032-2034 have the same pixel coordinates as the centroid 2026, which are designated as the centroid coordinates of the spot 2006 in each of the images 2002.

Figure 21:
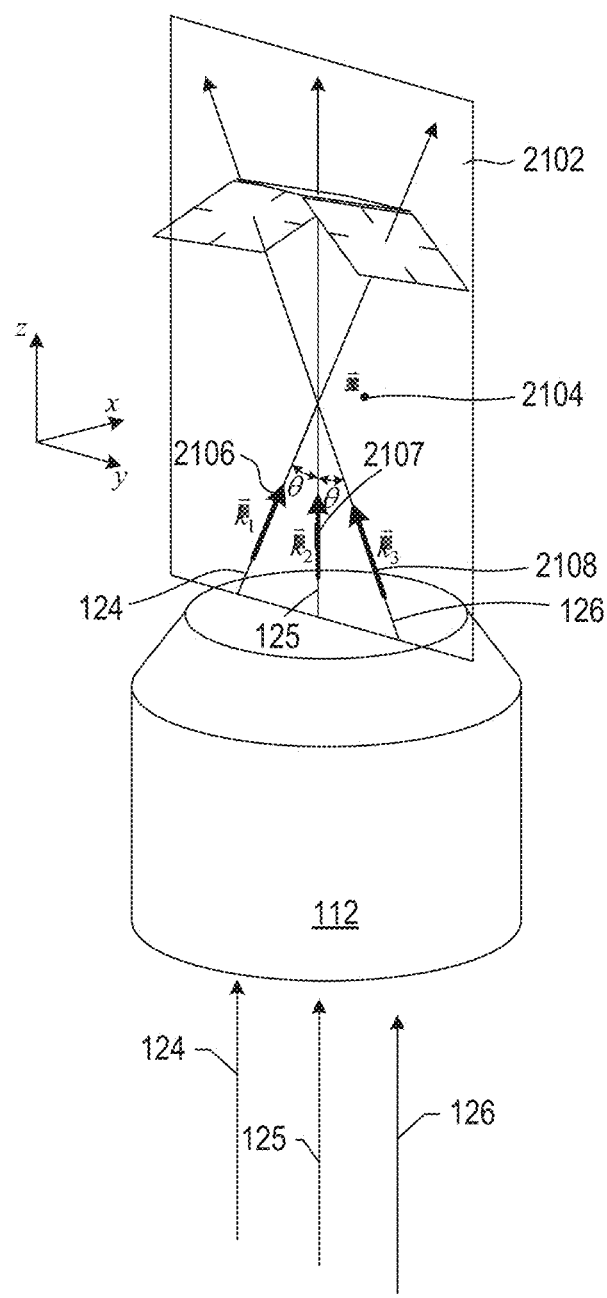
FIG. 21 shows an example of a two-dimensional surface defined by intersecting beams.

Each centroid coordinate in the filtered image 2022 is resolved to produce a resolved image by solving set of least squares equations for each centroid. For each of the three rotation angles, three plane waves interfere to produce the SIP, as described above with reference to FIG. 7. Each of the rotational angles is treated separately as a two-dimensional surface defined by the three intersecting beams 124-126. FIG. 21 shows an example of a two-dimensional surface 2102 defined by the intersecting beams 124-126. As the plane waves of the beams 124-126 propagate along the surface 2102, the plane waves accumulate phase. Thus, for one of the beams, each point $\vec{x}$ 2104 on the surface 2102 has a corresponding scalar phase. The other two beams similarly accumulate phase as the beams propagate in the y- and z-directions, but the phase at the point $\vec{x}$ 2104 on the surface is different for each of the three beams 124-126. The positions are two-dimensional vectors $\vec{x}$, as are the wave vectors $\vec{k}$ associated with each of the beams. The phases for the three beams at the point $\vec{x}$ 2104 are $\vec{k}_1 \cdot \vec{x}$, $\vec{k}_2 \cdot \vec{x}$, and $\vec{k}_3 \cdot \vec{x}$, where directional arrows 2106-2108 represent the corresponding wave vectors given by:

$$\vec{k}_1 = \frac{2\pi}{\lambda}(\cos\theta \hat{z} + \sin\theta \hat{y})$$

$$\vec{k}_2 = \frac{2\pi}{\lambda}\hat{z}$$

$$\vec{k}_3 = \frac{2\pi}{\lambda}(\cos\theta \hat{z} - \sin\theta \hat{y})$$

where $\lambda$ is the optical wavelength, $\theta$ is the angle between the side beams 124 and 126 and the optical axis or central beam 125, and $\hat{z}$ and $\hat{y}$ are unit vectors in the z- and y-directions. At the point $\vec{x}$ 2104, the beams 124-126 have complex amplitudes given by:

$$\exp(i\vec{k}_1 \cdot \vec{x}), \exp(i\vec{k}_2 \cdot \vec{x}), \text{ and } \exp(i\vec{k}_3 \cdot \vec{x})$$

The amplitudes of the three beams at the point $\vec{x}$ are summed and "squared" to obtain the intensity at the point $\vec{x}$ 2104 given by:

$$\left| \sum_{l=1}^{3} \exp(i\vec{k}_l \cdot \vec{x}) \right|^2$$

where |•| represents the absolute value or modulus of a complex number. Now suppose the SIP is moved K times and an image is captured after each move for a total of K+1 images as described above with reference to FIG. 20. The vector offsets, $\vec{p}_j$, are known for each image. The set of least square equations are given by:

$$\sum_{j=0}^{K} \left[ D_j - \left| \sum_{l=1}^{3} \exp(i\vec{k}_l \cdot (\vec{x} - \vec{p}_j)) \right|^2 \right]^2 = 0$$

where $\vec{x}$ represents the centroid coordinates of a spot, and $D_j$ is the normalized \count of the spot in the jth image. This set of equations can be solved numerically to obtain the coordinates (x, y, z) for the centroid in the resolved image. Note that the data consist of K+1 counts $D_j$ that correspond to the brightness of the fluorophore. The initial position of the SIP with respect to the fluorophore is regarded as unknown. Redundancies, such as multiple determinations of the axial position for multiple rotation angles, can serve as useful constraints.

An alternative to continuously computing field intensities and amplitudes in the image reconstruction program is to compute the field intensities once and store them as fine-meshed two-dimensional look-up tables. One method comprises computing a different look-up table for each of the offsets $\vec{p}_j$. The least-squares sum is minimized by varying the same two-dimensional index in each of the look-up tables.

Figure 22:
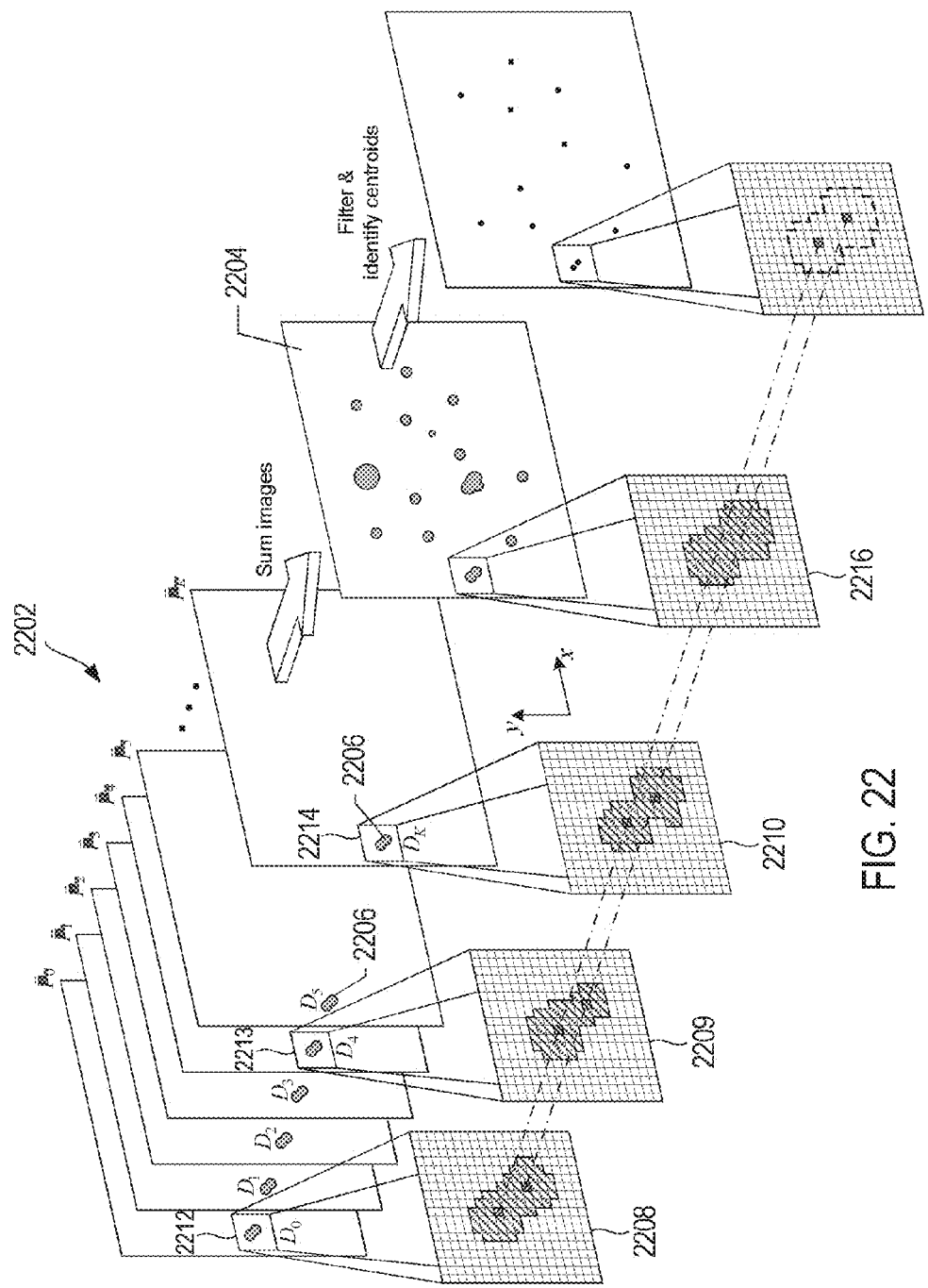
FIG. 22 shows a hypothetical series of images of a set of stochastically activated fluorophores of a sample specimen.

Method embodiments also include mathematical techniques for resolving the centroid locations of overlapping spots. When the signal from one nominally-resolved spot comprises signals from two nearby fluorophores the fit data is inconsistent and/or produces a weak fit, because contrast is reduced. In certain cases, two closely positioned fluorophores can be hypothesized, and the minimization described above can be used to find the two locations that produce the best fit. In general, the intensities of the two fluorophores may be part of the fit. FIG. 22 shows a hypothetical series of images 2202 of a set of stochastically activated fluorophores of a sample specimen. The images are captured in the same manner described above with reference to FIG. 20, except the images 2202 include overlapping spots 2206 that are common to the images 2202. The overlapping spots in each of images 2202 represents two closely spaced light-emitting fluorophore that are excited to some degree by the 3D-SIP. FIG. 22 includes magnified views 2208-2210 of subregions 2212-2214 of the images $\vec{p}_0$, $\vec{p}_4$, and $\vec{p}_K$, respectively. As described above with reference to FIG. 13, the images 2202 are summed to generate a summed image 2204. Shaded pixels in magnified view 2216 of a region 2218 represent the sum of the intensities of corresponding pixels associated with the overlapping spot 2206 in each of the images 2202.

For overlapping spots, such as the spot 2206 shown in FIG. 22, a different set of least square equations are used to compute the centroids of the overlapping spots:

$$\sum_{j=0}^{K} \left[ D_j - \left| \sum_{l=1}^{3} \exp(i\vec{k}_l \cdot (\vec{x}_1 - \vec{p}_j)) \right|^2 - \left| \sum_{l=1}^{3} \exp(i\vec{k}_l \cdot (\vec{x}_2 - \vec{p}_j)) \right|^2 \right]^2 = 0$$

where K is the number of images in the series of images 2202, $\vec{x}_1$ and $\vec{x}_2$ represent the centroid coordinates of the two neighboring spots, and $D_j$ is the normalized count of the overlapping spots in the jth image. Alternatively, $D_j$ is the normalized count associated with one of the spots. In practice, the neighboring spots may have different initial intensities $I_1$ and $I_2$. In this case, the set of least square equations used to compute the centroids of the overlapping spots is given by:

$$\sum_{j=0}^{K}\left[D_j - \left|I_1\sum_{l=1}^{3}\exp(i\vec{k}_l\cdot(\vec{x}_1 - \vec{p}_j))\right|^2 - \left|I_2\sum_{l=1}^{3}\exp(i\vec{k}_l\cdot(\vec{x}_2 - \vec{p}_j))\right|^2\right]^2 = 0$$

Figure 23:
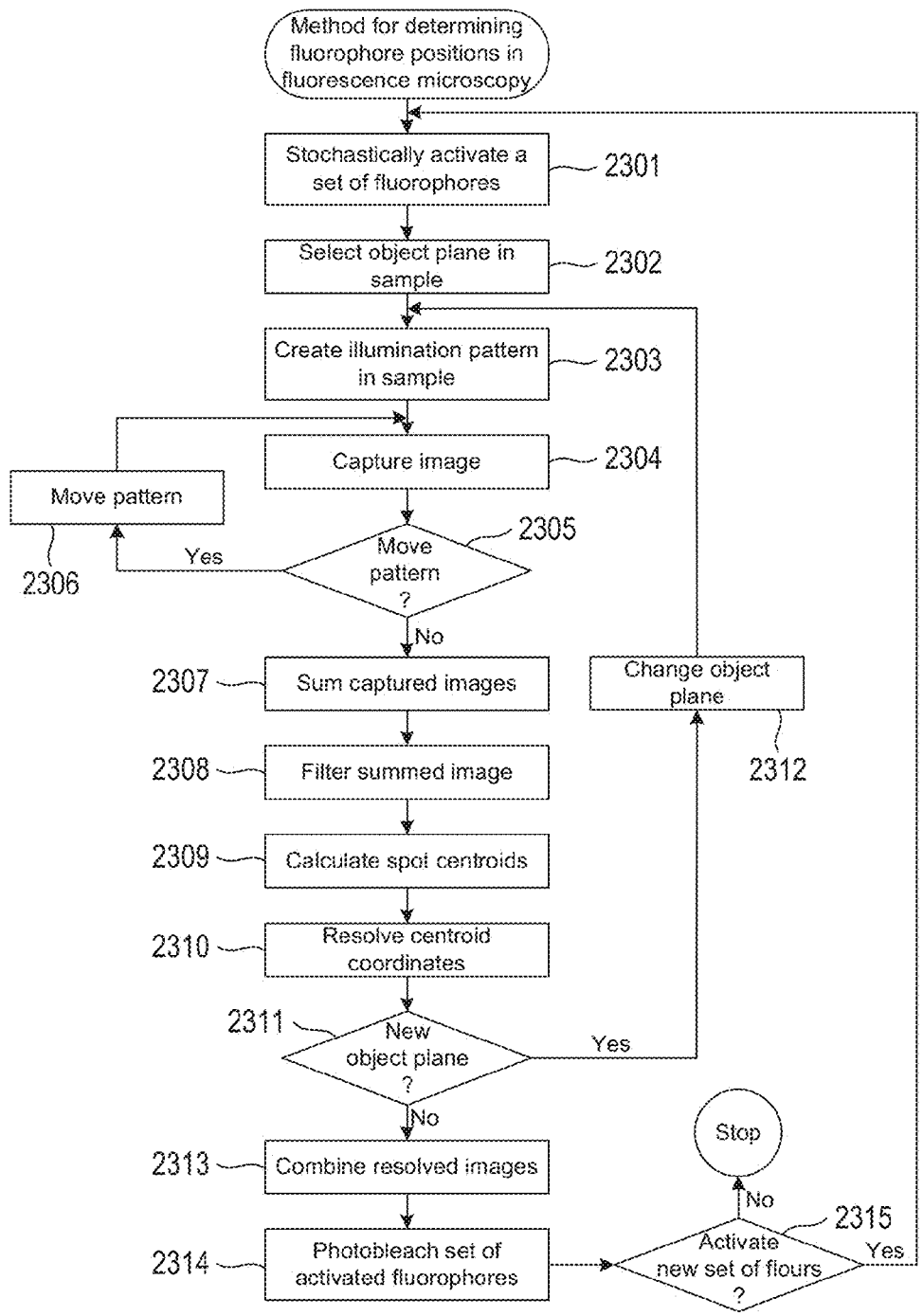
FIG. 23 shows a control-flow diagram of a computational method for determining and resolving fluorophore positions in fluorescence microscopy.

FIG. 23 shows a control-flow diagram of a computational method for determining and resolving fluorophore positions in fluorescence microscopy. In block 2301, a sample specimen is illuminated with a weak intensity beam of activation light in order to stochastically activate a limited and spatially distributed number of fluorophores, as described above with reference to FIG. 1. In block 2302, a focal plane within the sample is selected by setting the focus of the objective lens. In block 2303, a 3D-SIP of excitation light is created within the sample and centered on the focal plane, as described above with reference to FIGS. 1 and 7-11. Blocks 2304-2306 represent the process of capturing images of the light-emitting fluorophores as the 3D-SIP is stepped through lateral and axial positions and may also be rotated, as described above with reference to FIGS. 8, 9, 11, and 12 to generate a series of images. In block 2304, an image of fluorescing, activated fluorophores in the sample is captured and stored. In block 2305, when the 3D-SIP is to be stepped or rotated to a different position within the sample, the method proceeds to block 2306. Otherwise, the method proceeds to block 2307. In block 2306, the 3D-SIP is stepped through lateral and axial positions as described above with reference to FIGS. 8 and 9, and the 3D-SIP may be rotated, as described above with reference to FIGS. 11 and 12. In block 2307, the series of images are summed to form a summed image, as described above with reference to FIGS. 13 and 20. In block 2308, the summed image is filtered to remove spots that are either larger than or less than maximum and minimum diameter thresholds and to remove irregularly shaped spots to produce a filtered image. In block 2309, the centroids of spots remaining in the filtered image are calculated as described above with reference to FIG. 14. In block 2310, centroid coordinates of the centroids in the filtered image are resolved to generate a resolved image, as described above with reference to FIGS. 16, 17, 20, and 22. In block 2311, when a new object plane (i.e., z-coordinate) of the sample is to be focused on, the method proceeds to block 2312, otherwise, the method proceeds to block 2313. In block 2312, a new object plane within the sample can be selected by changing the focus of the objective lens, and the processes associated with the blocks 2303-2311 are repeated for the new object plane. In block 2313, the resolved are image are combined to generate a super-resolution image of the activated fluorophores in the object plane, as described above with reference to FIG. 18. In block 2314, the activated fluorophores can be photobleached as described above with reference to FIG. 1. In block 2315, when a new set of fluorophores are to be activated, the method repeats the processes associated with blocks 2301-2314, otherwise, the method stops.

Figure 24:
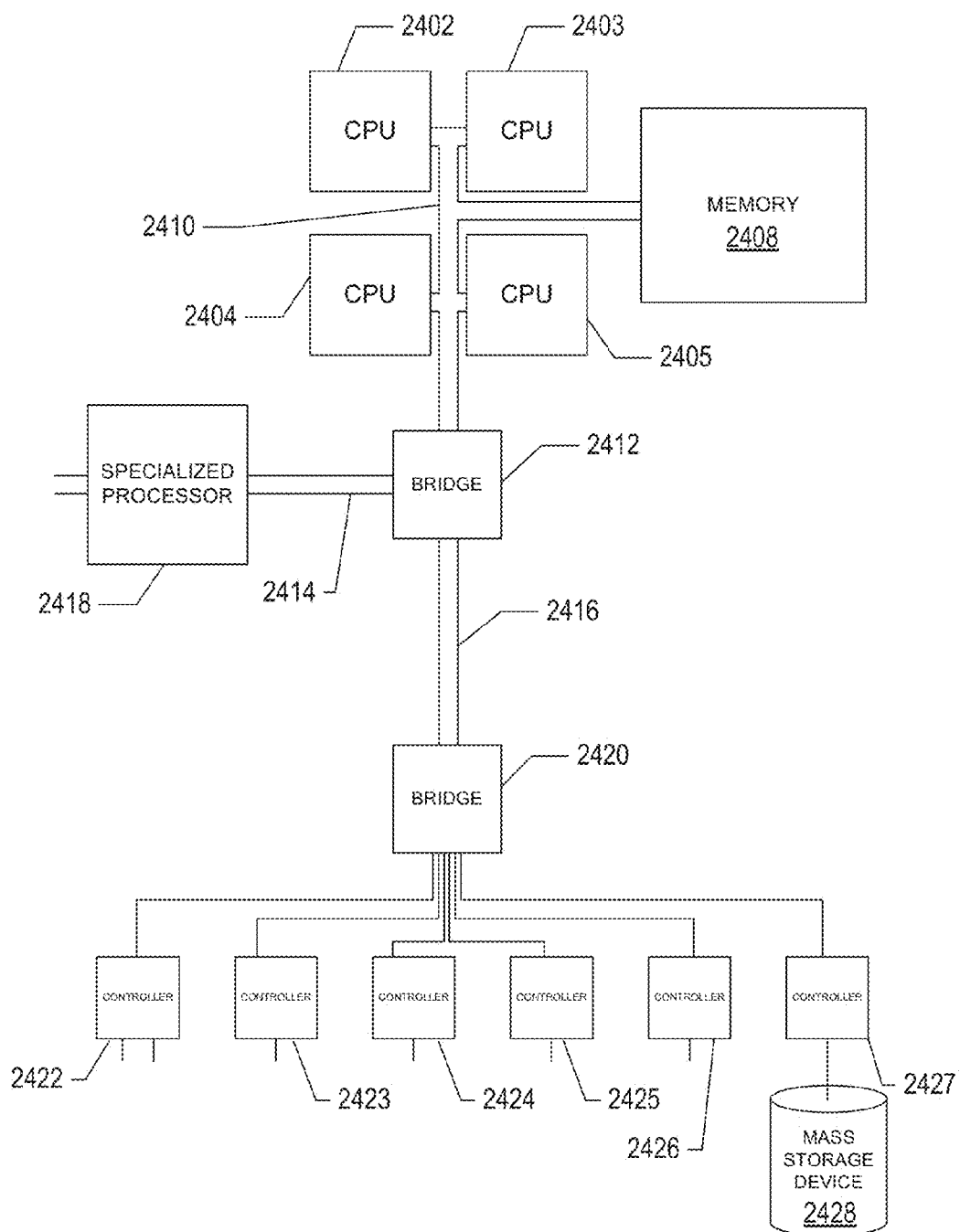
FIG. 24 shows an example of a computer system that executes an efficient method for determining super-resolution images of a sample specimen.

FIG. 24 shows one illustrative example of the computer system 144 of FIG. 1 that executes an efficient method for determining super-resolution images of sample specimen. The internal components of many small, mid-sized, and large computer systems as well as specialized processor-based storage systems can be described with respect to this generalized architecture, although each particular system may feature many additional components, subsystems, and similar, parallel systems with architectures similar to this generalized architecture. The computer system contains one or multiple central processing units ("CPUs") 2402-2405, one or more electronic memories 2408 interconnected with the CPUs by a CPU/memory-subsystem bus 2410 or multiple busses, a first bridge 2412 that interconnects the CPU/memory-subsystem bus 2410 with additional busses 2414 and 2416, or other types of high-speed interconnection media, including multiple, high-speed serial interconnects. These busses or serial interconnections, in turn, connect the CPUs and memory with specialized processors, such as a graphics processor 2418, and with one or more additional bridges 2420, which are interconnected with high-speed serial links or with multiple controllers 2422-2427, such as controller 2427, that provide access to various different types of computer-readable media, such as computer-readable medium 2428, electronic displays, input devices, and other such components, subcomponents, and computational resources. The electronic displays, including visual display screen, audio speakers, and other output interfaces, and the input devices, including mice, keyboards, touch screens, and other such input interfaces, together constitute input and output interfaces that allow the computer system to interact with human users. Computer-readable medium 2428 is a data-storage device, such as electronic memory, optical or magnetic disk drive, USB drive, flash memory and other such data-storage device. The computer-readable medium 2428 can be used to store machine-readable instructions and can be used to store encoded data, during store operations, and from which encoded data can be retrieved, during read operations, by computer systems, data-storage systems, and peripheral devices. The machine-readable instructions execute the methods described above and operate the light sources and objective lens.

In order to optimize speed and minimize computational requirements, as few images as possible can be recorded by increasing active fluorophore spatial density in each image to as high as can be tolerated. By using an increased number of active fluorophores it is more likely that corresponds spots will overlap in the image plane and cannot be distinguished with diffraction-limited optics. For example, when a given spot gives inconsistent or unsatisfactory multiple cosine and sine vector products, the spot is identified.

Note that activated fluorophores may be prematurely turned "off" or even "blink." Because the methods described herein include redundant measurements of axial positions, inconsistent results for a single fluorophore can be identified and the fluorophore discarded from the image data.

EXPERIMENTAL RESULTS

Monte Carlo test in MatLab using least squares fits with overlapping response curves on axially overlapping simulated data were performed.

Figure 25A:
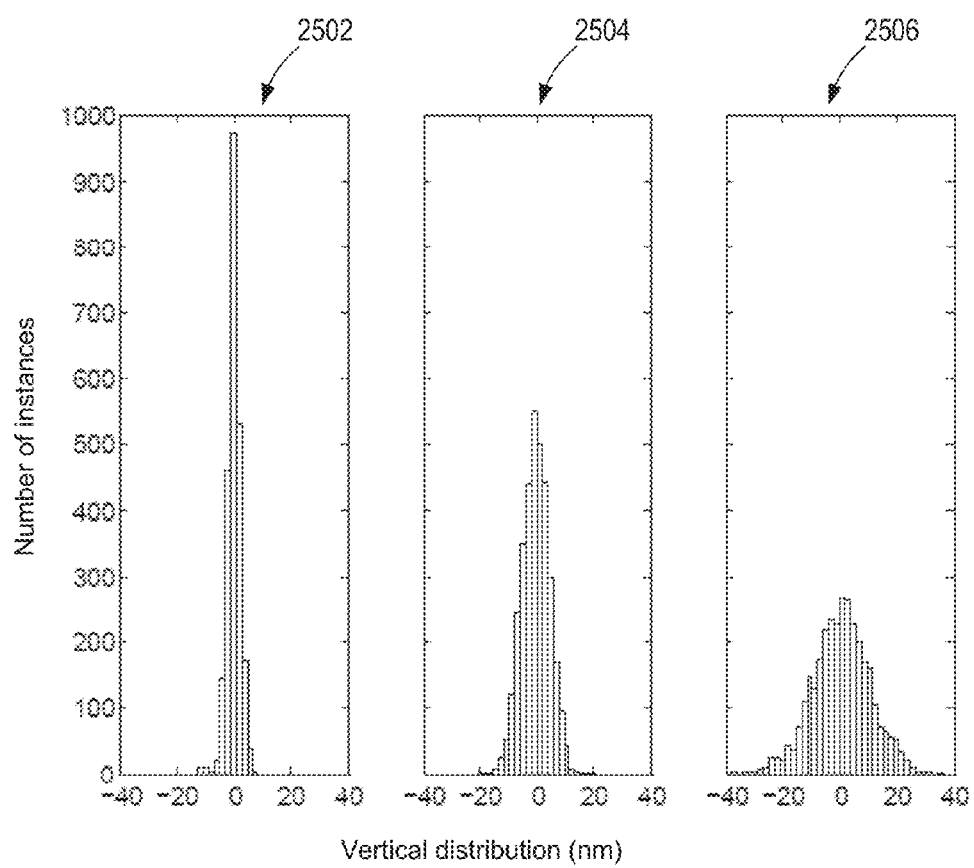
FIGS. 25A-25E show plots of results from experiments and simulations.

FIG. 25A shows results from a Monte Carlo study showing expected 3D-SIM localization distributions versus the total number of images received for each fluorophore spread over 10 images, between which the 3D-SIP is stepped axially a tenth of a period. The Monte Carlo data in FIG. 25A were processed from artificial image stacks. Image stacks were processed in MatLab, and spots in the sum image where identified automatically with the MatLab "bwareopen" function. The SIP was stepped axially by $P_A/10$ through 10 vertical levels, and stepped laterally by $P_L/5$ for 5 steps at each vertical level, for a total of 50 images. The data were processed via the sine-cosine vector multiplication method described above with reference to FIG. 20. Spot centroids were generated at random, and the read noise and shot noise effects were incorporated into Gaussian spot pixel geometries. Lateral resolutions are comparable. Nine pixels were summed for each spot in each image, and shot and read noise are included. For the first panel 2502, 1000 electrons are distributed over the 10 images, with the full-width at half-maximum ("FWHM") equal to pitch/40. CCD and CMOS detectors measure the number of electrons excited into the conduction band by photons. Quantities, such as shot noise, depend on the number of electrons, not the number of counts. The system-dependent factor "electrons per count" can be determined using a well-known photon transfer curve. For second panel 2504, 300 electrons are distributed over the 10 images, with FWHM equal to pitch/25. For third panel 2506, 100 electrons are distributed over the 10 images, with FWHM equal to pitch/15. The methods described herein are robust, delivering super-resolved three-dimensional location information even with very few (e.g., 100) detected electrons distributed through the image stack.

Figure 25B:
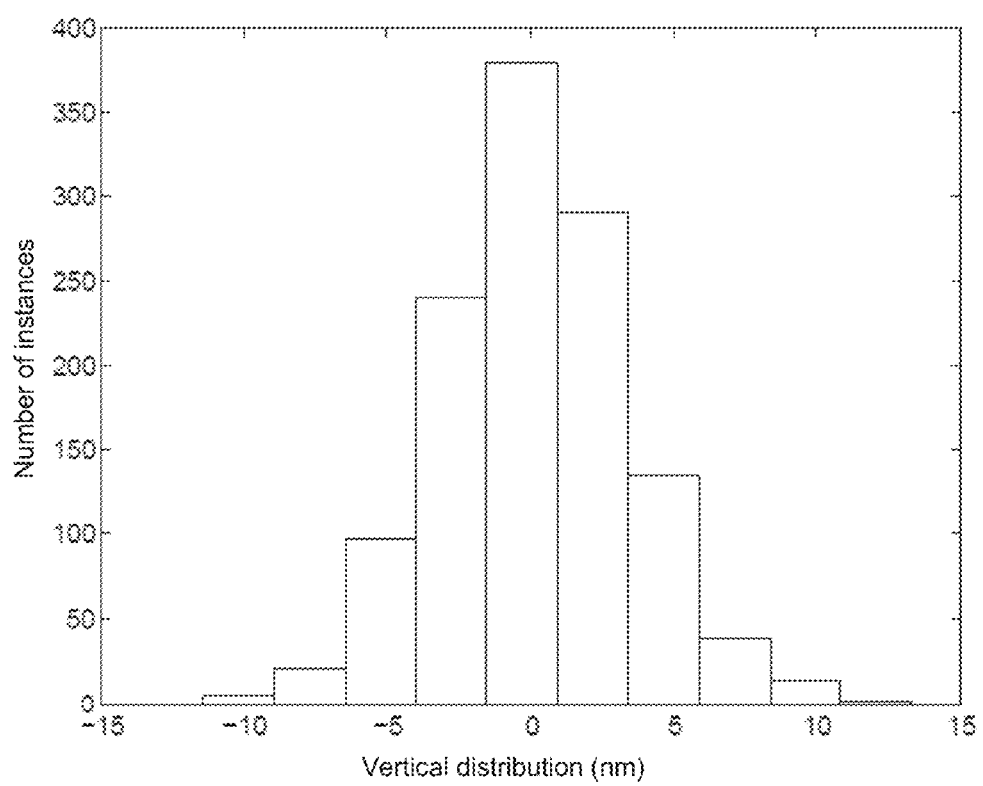
Figure 25C:
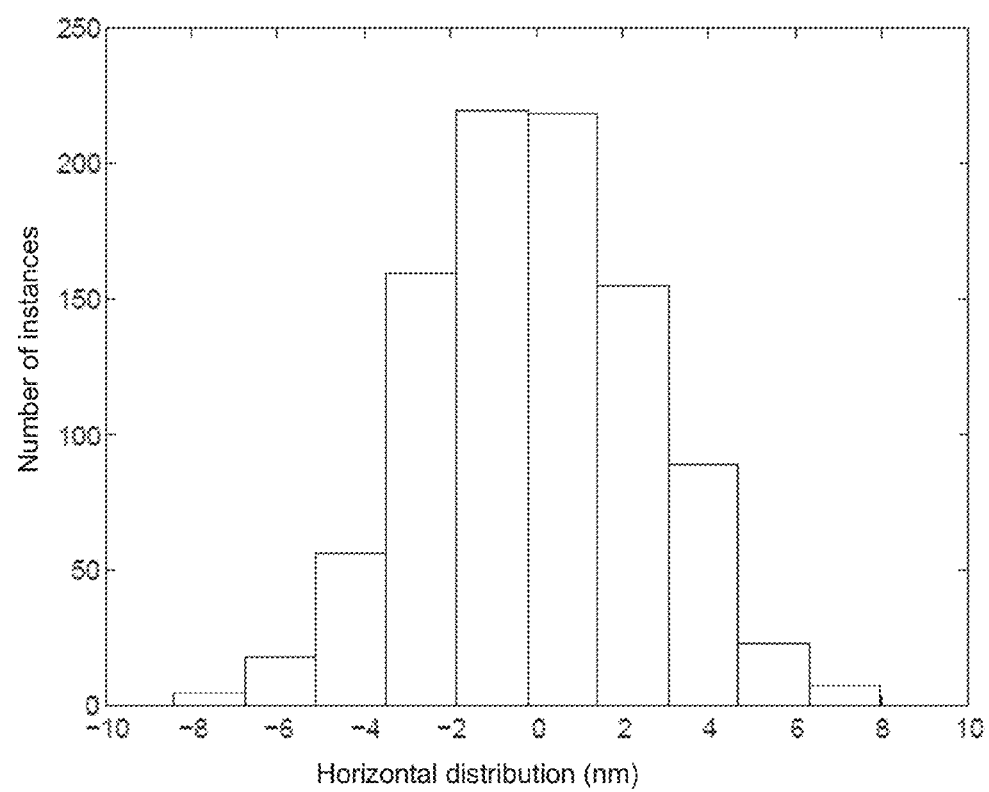

FIGS. 25B and 25C are data from actual images obtained using green 100 nm fluorescent beads illuminated by a SIP at 488 nm. Image stacks were processed in MatLab, and spots in the sum image where identified automatically with the MatLab "bwareaopen" function. The SIP was stepped axially by $P_A/10$ through 10 vertical levels, and stepped laterally by $P_L/5$ for 5 steps at each vertical level, for a total of 50 images. The data were processed via the sine-cosine vector multiplication method described above with reference to FIG. 20. For each fluorophore of the five lateral steps, two yielded the strongest vertical modulation signals. These two scans reported similar modulation strength but opposite phases. The two scans observe the same fluorophore but are effectively independent experiments, therefore, it is meaningful to compare their results. If there were no errors, the results would be exactly 180 degrees out of phase. FIGS. 25B and 25C plots the distribution of differences from 180 degrees, which are scaled by the SIP pitch into nanometers. In both cases, the FWHM of the distributions are well under 10 nm, which demonstrates the power of the technique. In particular, FIG. 25B shows a histogram of an axial distribution of fluorescent bead locations for 50 images obtained using 10 axial steps and 5 lateral steps. The data was obtained using a sample composed of 1205 100 nanometer fluorescent beads. Two phases, approximately 180 degrees out of phase are subtracted and the mean is subtracted to center the histogram about zero. FWHM of the distributions is approximately 7 nanometers, which is approximately twice the standard deviation. FIG. 25C shows a histogram of a lateral distribution of the same beads represented in FIG. 25B. The lateral distribution is nearly the same as the axial distribution presented in FIG. 25B.

Figure 25D:
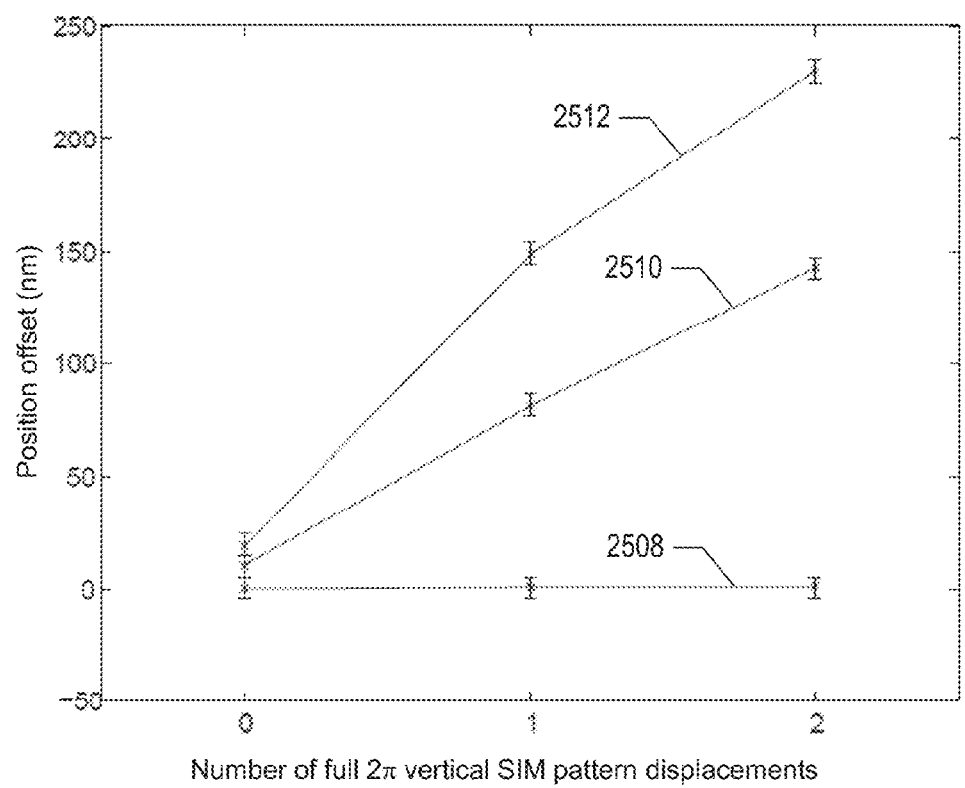

FIG. 25D shows a plot of position offset in nanometers versus the number of full $2\pi$ vertical 3D-SIP displacements. The results were obtained by scanning with only a single pitch and the results in $2\pi$-phase ambiguities as represented by curve 2508. However, rescanning the same sample but with the pitch of the three-dimension field lengthened by 2% gives position offset represented by curve 2510, and when the pitch of same 3D-SIP was lengthened by 4% the position offset was even greater as represented by curve 2512. The curves 2508, 2510, and 2512 indicate that the apparent position generally changes with changes in the pitch even in the first 3D-SIP (displacement 0), and the differences between displacements are distinguishable.

Figure 25E:
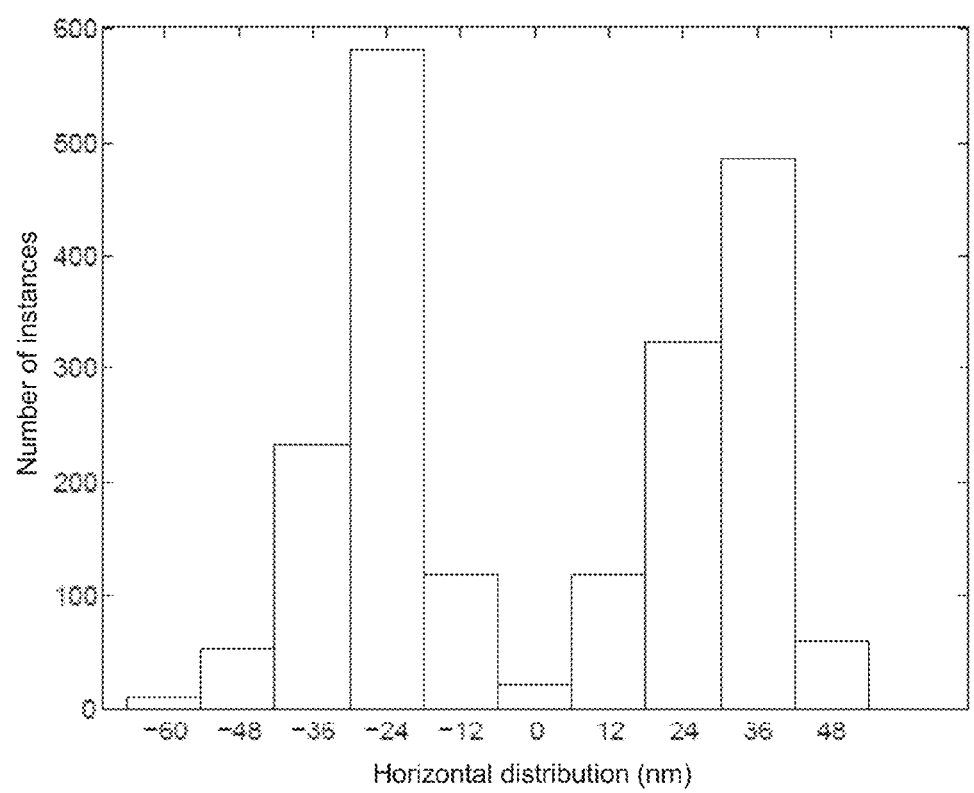

FIG. 25E shows a histogram of two fluorescent beads separated by 56 nanometers. A Monte Carlo study distinguished the nearby fluorophores in the z-direction by testing a two-fluor hypothesis by fitting the data for two modulated fluorophore. An isolated fluorescent bead fails the two-fluorophore hypothesis. The results of FIG. 25E did not use artificial image stacks, but were an analysis of Monte Carlo modulation data vectors The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. Obviously, many modifications and variations are possible in view of the above teachings. For example, rather than changing the focus of the objective lens 112 to change the z-coordinate as described above, the stage 111 of the microscope can be moved along the optical axis to create substantially the same change in the z-coordinate.

The examples are shown and described in order to best explain the principles of this disclosure and practical applications, to thereby enable others skilled in the art to best utilize this disclosure and various examples with various modifications as are suited to the particular use contemplated.

It is intended that the scope of this disclosure be defined by the following claims and their equivalents:

1. A method for determining coordinate positions of light-emitting particles that label at least one component of a sample specimen using a light microscope, the method comprising:
    activating a subset of the light-emitting particles by illuminating the sample with an activation light beam;
    capturing a series of images of the light emitted from the subset of particles illuminated with an excitation light beam forming a three-dimensional structured illumination pattern;
    generating a resolved image of the light-emitting particles from the series of images; and
    repeatedly activating, capturing, and generating to obtain a number of resolved images that are processed to obtain a super-resolution image of the at least one component, wherein the super-resolution image has a higher resolution than a diffraction limit of the light microscope,
    wherein illuminating the sample with the activation light beam further comprises illuminating the sample with the activation light beam that stochastically activates the subset of light-emitting particles, and
    wherein generating the resolved image further comprises:
    summing the series of images to generate a summed image of the each subset of particles;
    determining centroid positions of the each subset of particles in the summed image; and
    resolving centroid positions in the summed image to generate the resolved image.

2. The method of claim 1, wherein capturing the series of images further comprises generating the illumination pattern from at least three beams of coherent excitation light transmitted through an objective lens to intersect within the sample.

3. The method of claim 1, wherein capturing the series of images further comprises changing a position of the illumination pattern prior to capturing each image in the series.

4. The method of claim 3, wherein changing the position of the illumination pattern further comprises rotating the illumination pattern.

5. The method of claim 3, wherein changing the position of the illumination further comprises translating the illumination pattern.

6. The method of claim 1, further comprises photobleaching the subset of light-emitting particles in the activated state.

7. The method of claim 1, wherein generating the resolved image further comprises:
summing the series of images to generate a summed image of spots;
determining centroid positions of the spots; and
resolving spot centroid positions to generate the resolved image.

8. The method of claim 1, further comprises discarding image data associated with inconsistent image results for single fluorophores.

9. The method of claim 1, wherein the number of resolved images are processed to obtain the super-resolution image further comprising summing the resolved images to generate the super-resolution image.

10. The method of claim 1, wherein each image of the series of images is identified by a lateral and an axial step the three-dimensional structured illumination is in at the time the each image is captured.

11. A method for generating a super-resolution image of a sample specimen using a light microscope, the method comprising:
separately activating different subsets of light-emitting particles attached to components of the sample by illuminating the sample with an activation light beam;
generating a series of images for each subset of activated particles by repeatedly illuminating the sample with an excitation light beam forming a three-dimensional structured illumination pattern and capturing an image of the light emitted from the subset of particles illuminated with the illumination pattern in different positions within the sample;
combining the series of images to generate a resolved image for each subset of particles; and
combining the resolved images to generate a super-resolution image of the sample, wherein the super-resolution image has a higher resolution than a diffraction limit of the light microscope,
wherein illuminating the sample with the activation light beam further comprises illuminating the sample with the activation light beam that stochastically activates the subset of light-emitting particles, and
wherein generating the resolved image further comprises:
summing the series of images to generate a summed image of the each subset of particles;
determining centroid positions of the each subset of particles in the summed image; and
resolving centroid positions in the summed image to generate the resolved image.

12. The method of claim 11, wherein illuminating the sample with the excitation light beam forming a three-dimensional structured illumination pattern further comprises interfering at least three beams of coherent excitation light that passes through an objective lens to intersect within the sample.

13. The method of claim 11, wherein capturing the image of the light emitted from the subset of particles illuminated with the illumination pattern in different positions further comprises rotating the illumination pattern.

14. The method of claim 11, wherein capturing the image of the light emitted from the subset of particles illuminated with the illumination pattern in different positions further comprises translating the illumination pattern to a different lateral position for each image.

15. The method of claim 11, wherein capturing the image of the light emitted from the subset of particles illuminated with the illumination pattern in different positions further comprises moving the illumination pattern to a different axial position for each image.

16. The method of claim 11, further comprises photobleaching each subset of light-emitting particles in an activated state after each resolved image is generated.

17. The method of claim 11, wherein generating the resolved image further comprises:
summing the series of images to generate a summed image of spots;
determining centroid positions of the spots; and
resolving spot centroid positions to generate the resolved image.

18. The method of claim 11, further comprises discarding image data associated with inconsistent image results for single fluorophores.

19. The method of claim 11, wherein combining the resolved images to generate the super-resolution image further comprising summing the resolved images.

* * * * *